United States Patent [19]

Bruno et al.

[11] Patent Number: 6,013,622
[45] Date of Patent: Jan. 11, 2000

[54] METHOD OF REGULATING APPETITE AND METABOLISM

[75] Inventors: John F. Bruno, Centereach, N.Y.; Jeffrey White, Bridgewater, N.J.; Michael Berelowitz, New York, N.Y.; Daniel Tripodi, Lebanon, N.J.; Matthew Heil, Danbury, Conn.

[73] Assignees: Nutriceutical Technology Corporation, Bridgewater, N.J.; Research Foundation of State University of New York, Stony Brook, N.Y.

[21] Appl. No.: 09/060,437

[22] Filed: Apr. 15, 1998

[51] Int. Cl.$^7$ .................................................. A61K 31/00
[52] U.S. Cl. .................................. 514/2; 514/21; 514/23; 514/414; 514/440; 514/909; 426/72; 426/656; 426/658
[58] Field of Search .................................. 514/2, 21, 23, 514/414, 440, 209; 426/72, 656, 658

[56] References Cited

U.S. PATENT DOCUMENTS 5,480,865   1/1996   Kingham et al. .......................... 514/2

OTHER PUBLICATIONS

D. Larhammar, "Evolution of neuropeptide Y, peptide YY and pancreatic polypeptide," *Regulatory Peptides*, 62:1–11 (1996).

White, "Neuropeptide Y: a central regulator of energy homeostasis," *Regulatory Peptides*, 49:93–107 (1993).

Sanacora et al., "Increased hypothalamic content of preproneuropeptide Y messenger ribonucleic acid in genetically obese Zucker rats and its regulation by food deprivation," *Endocrinology*, 127(2):730–737 (1990).

Sanacora et al., "Developmental aspect of differences in hypothalamic preproneuropeptide Y messenger ribonucleic acid content in lean and genetically obese Zucker rats," *J. Neuroendocrinol.*, 4(3):353–357 (1990).

White and Kershaw, "Increase hypothalamic neuropeptide Y expression following food deprivation," *Molec. & Cell. Neurosci.*, 1:41–48 (1990).

Sahu, et al. "Neuropeptide Y gene expression in rats on scheduled feeding regimen," *Molecular Brain Research*, 15:15–18 (1992).

Berelowitz et al., "Regulation of hypothalamic neuropeptide expression by peripheral metabolism," *TEM* 3(4):127–133 (1992).

White et al., "Localization of prepro–growth hormone releasing factor mRNA in rat brain and regulation of its content by food deprivation and experimental diabetes," *Molec. & Cell. Neurosci.*, 1:183–192 (1990).

Bruno et al., "Influence of food deprivation in the rat on hypothalamic expression of growth hormone–releasing factor and somatostatin," *Endocrinology*, 127(5):2111–2116 (1990).

NIH Technology Assessment Conference Panel, "Methods for voluntary weight loss and control," *Ann. Intern. Med.*, 116:942–949 (1992).

Wadden, "Treatment of Obesity by moderate and severe caloric restriction," *Ann. Intern. Med.*, 119:688–693 (1993).

Bruno et al., "Regulation of rat hypothalamic preprogrowth hormone–releasing factor messenger ribonucleic acid by dietary protein," *Endorcinology*, 129(3):1226–1232 (1991).

Bruno et al., "Regulation of hypothalamic preprogrowth hormone–releasing factor messenger ribonucleic acid expression in food–deprived rats: A role for histaminergic neurotransmission," *Endocrinology*, 133(3):1377–1381 (1993).

Latham and Blundell, "Evidence for the effect of tryptophan on the pattern of food consumption in free feeding and food deprived rats," *Life Sciences*, 24:1971–1978 (1979).

E. Jéquier, "Energy, obesity, and body weight standards," *Am. J. Clin. Nutr.*, 45:1035–47 (1987).

C. Dieguez, M.D. Page and M.F. Scanlon, "Growth hormone neuroregulation and its alterations in disease states," *Clinical Endocrinology*, 28:109–143 (1988).

Katch and McArdle: *Nutrition, Weight Control, and Exercise*, 3rd ed., Lea & Ferbiger, Philadelphia (1988).

M. Berelowitz et al., "Effects of growth hormone excess and deficiency on hypothalamic somatostatin content and release and on tissue somatostatin distribution," *Endocrinology* 109:714–719 (1981).

J.D. White et al., "Measurement of neuroendocrin peptide mRNA in discrete brain regions," *Methods in Enzymology*, P.M. Conn (Ed.), Academic Press, Orlando, FL, 124:548–560 (1986).

H. Higuchi et al., "Rat neuropeptide Y precursor gene expression," *J. Biol. Chem.* 263:6288–6295 (1988).

J.F. Bruno et al., "Regulation of rat hypothalamic preprogrowth hormone–releasing factor messenger ribonucleic acid by dietary protein," *Endocrinology* 129(3):1226–1232 (1991).

K.E. Mayo et al., "Characterization of cDNA and genomic clones encoding the precursor to rat hypothalamic growth hormone–releasing factor," *Nature* 314:464–467 (1985).

J.D. White et al., "Increased Hypothalamic Content of Preproneuropeptide–Y Messenger Ribonucleic Acid in Streptozotocin–Diabetic Rats," 126(2):765–772 (1990).

P. Ponsalle et al., "Glucocorticoids are Required for Food Deprivation–Induced Increases in Hypothalamic Neuropeptide Y Expression," 4(5):585–591 (1993).

*Primary Examiner*—James H. Reamer
*Attorney, Agent, or Firm*—Akin, Gump, Strauss, Hauer & Feld, L.L.P.

[57] ABSTRACT

Methods and compositions capable of controlling weight in an animal, preferably a human, which methods involve administering diet compositions that modulate, and preferably reduce, synthesis and secretion of neuropeptide Y (NPY) and modulate, and preferably increase synthesis and secretion of growth hormone releasing factor (GRF), compared to pre-administration amounts in the animal. The administration of such diet compositions results in a reduced appetite and a regulated metabolism that enhance weight control, including weight loss and reduction of obesity.

32 Claims, 13 Drawing Sheets

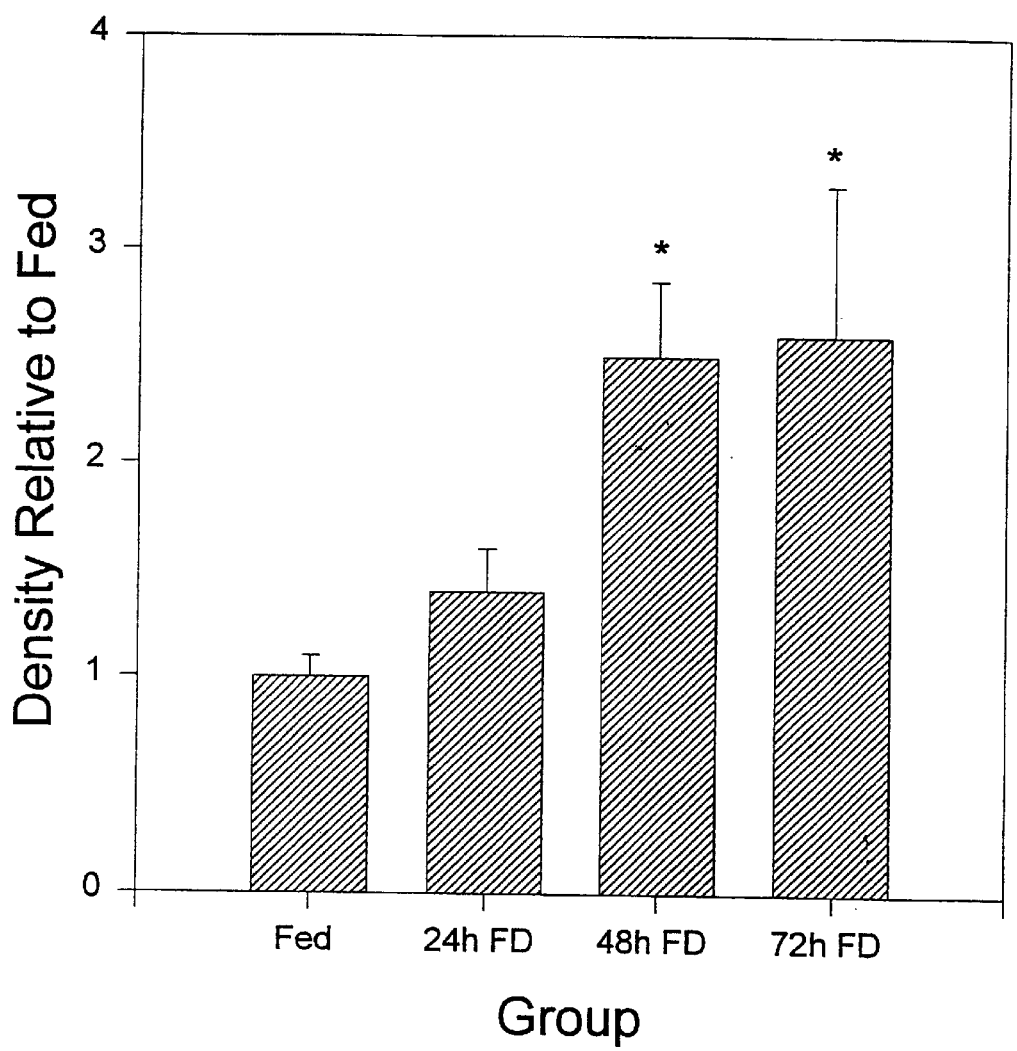
Fig. 1 Hypothalamic PreproNPY mRNA-Food Deprivation Time Course

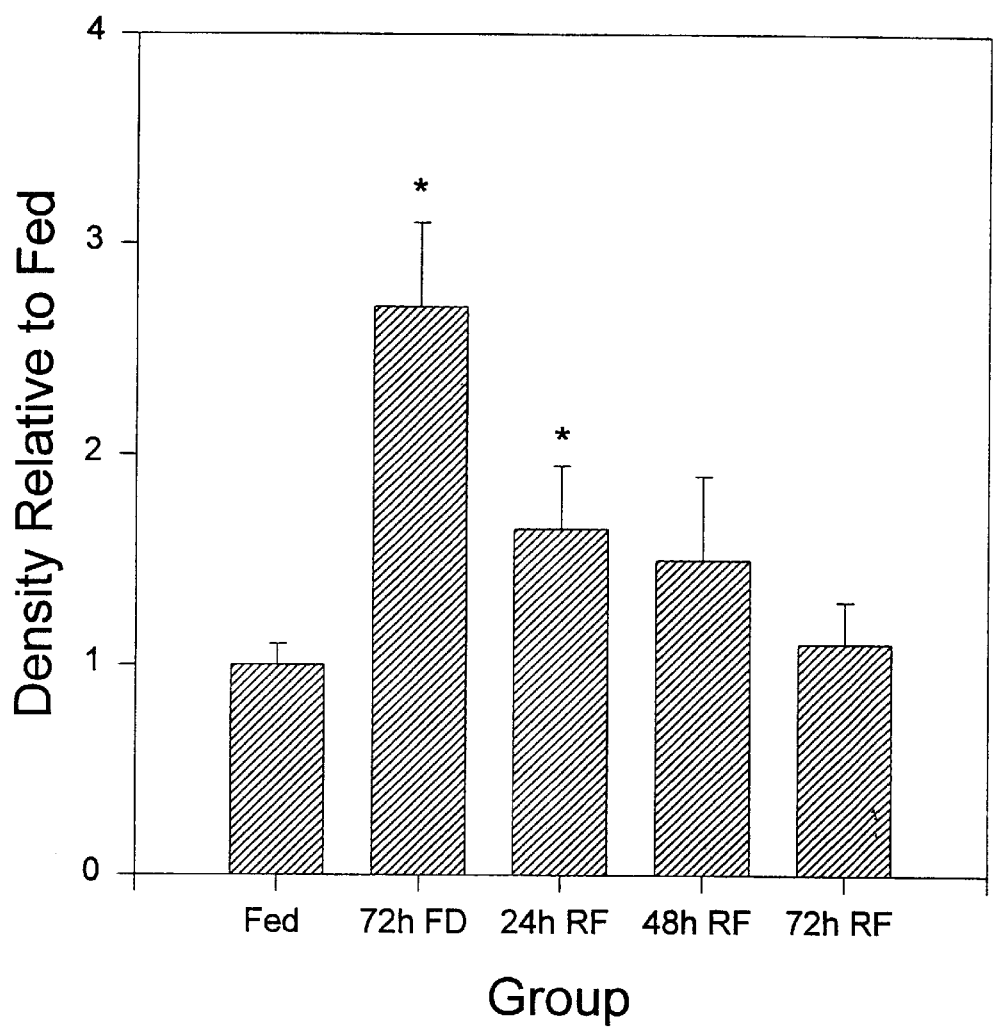

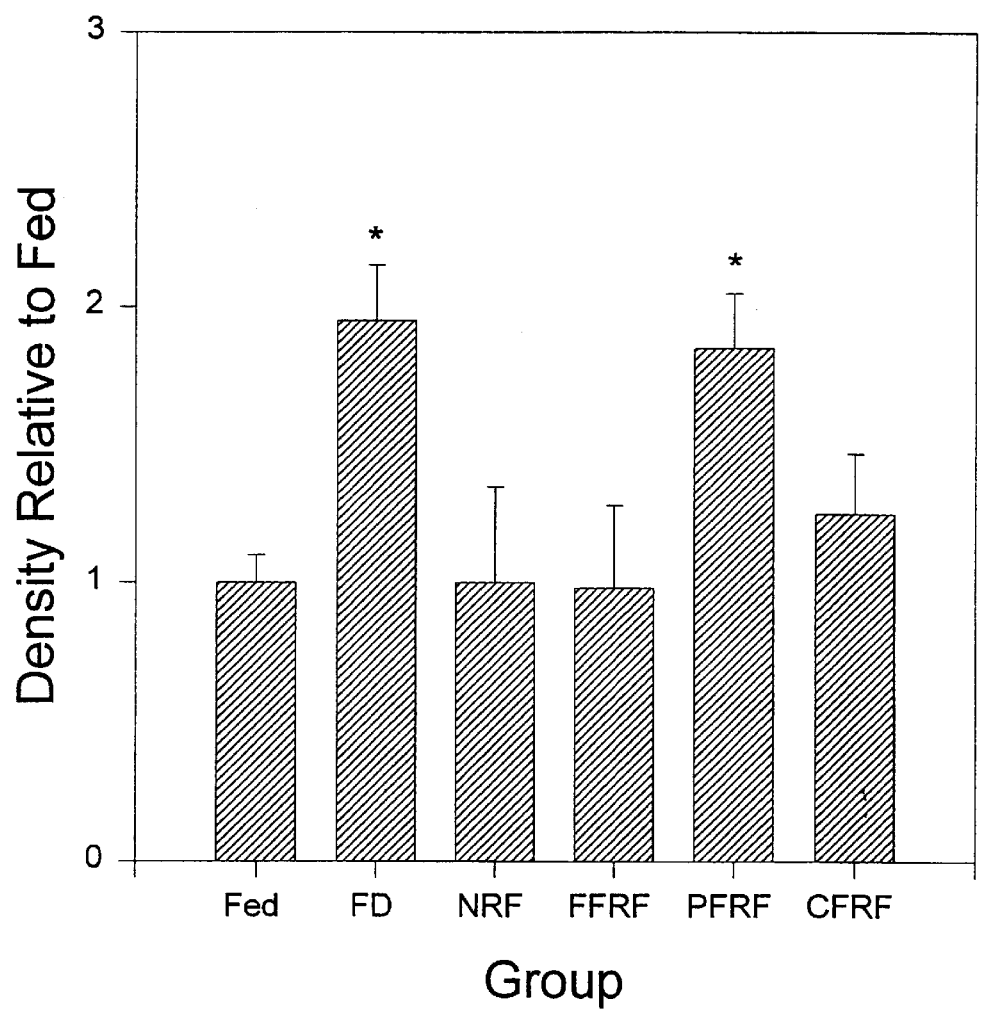
Fig. 3 Hypothalamic PreproNPY mRNA- Select Nutrient Refeeding

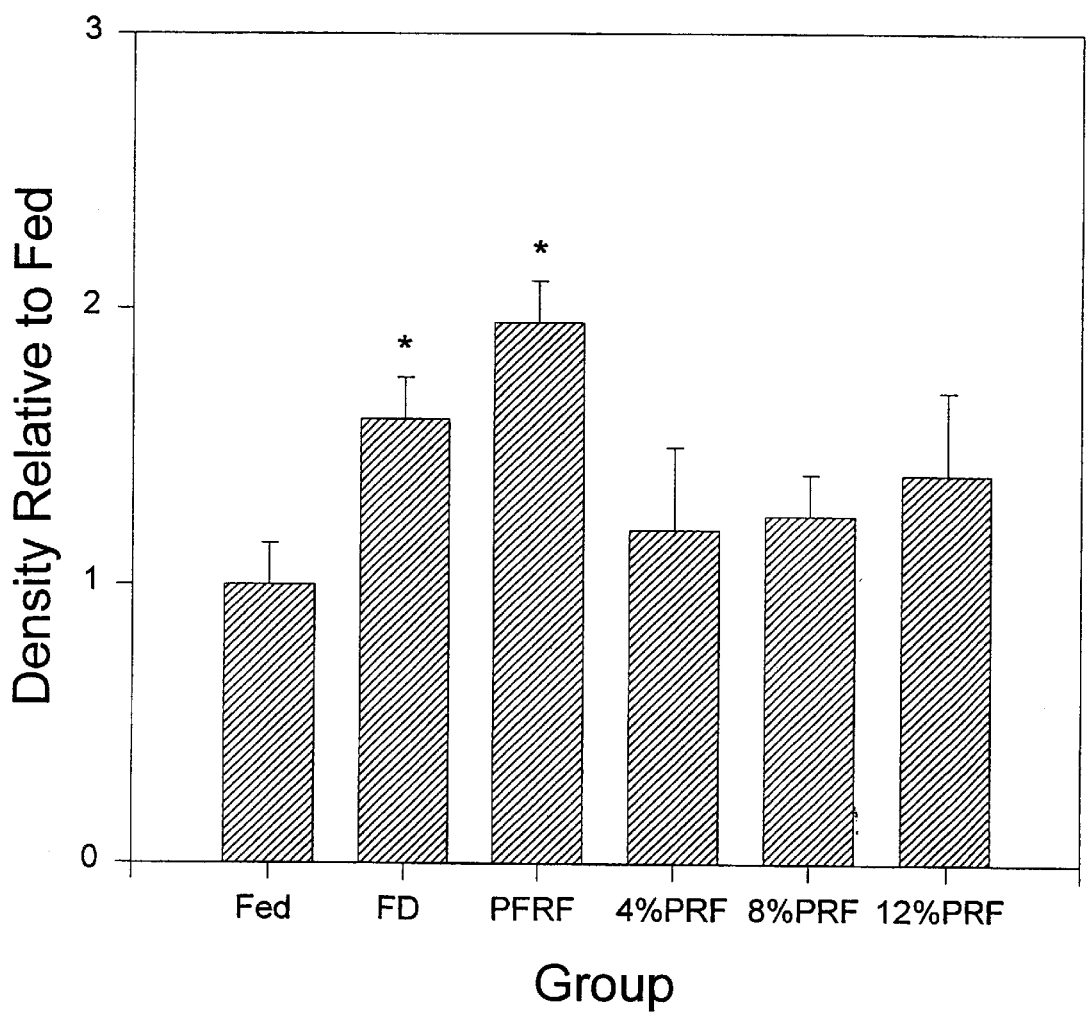
Fig. 4 Hypothalamic PreproNPY mRNA-Graded Protein Refeeding

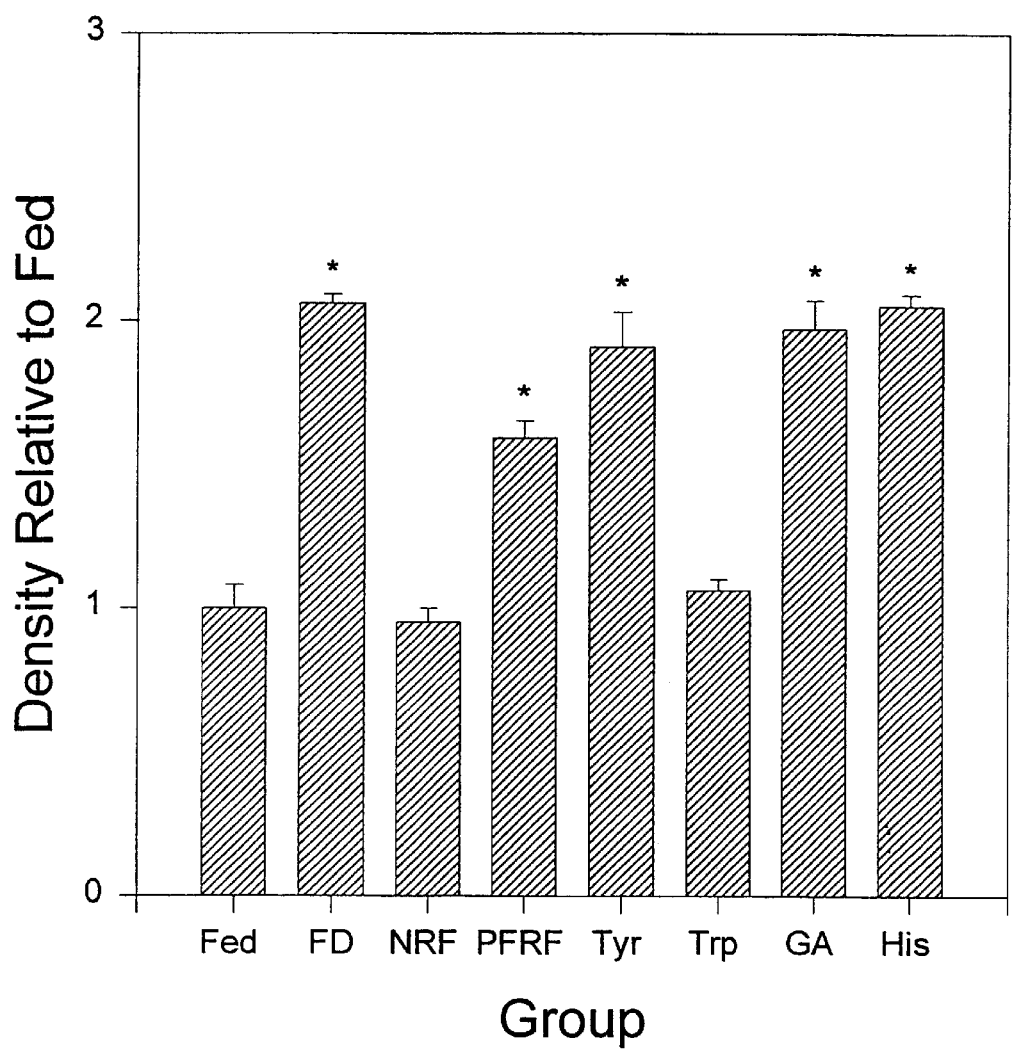

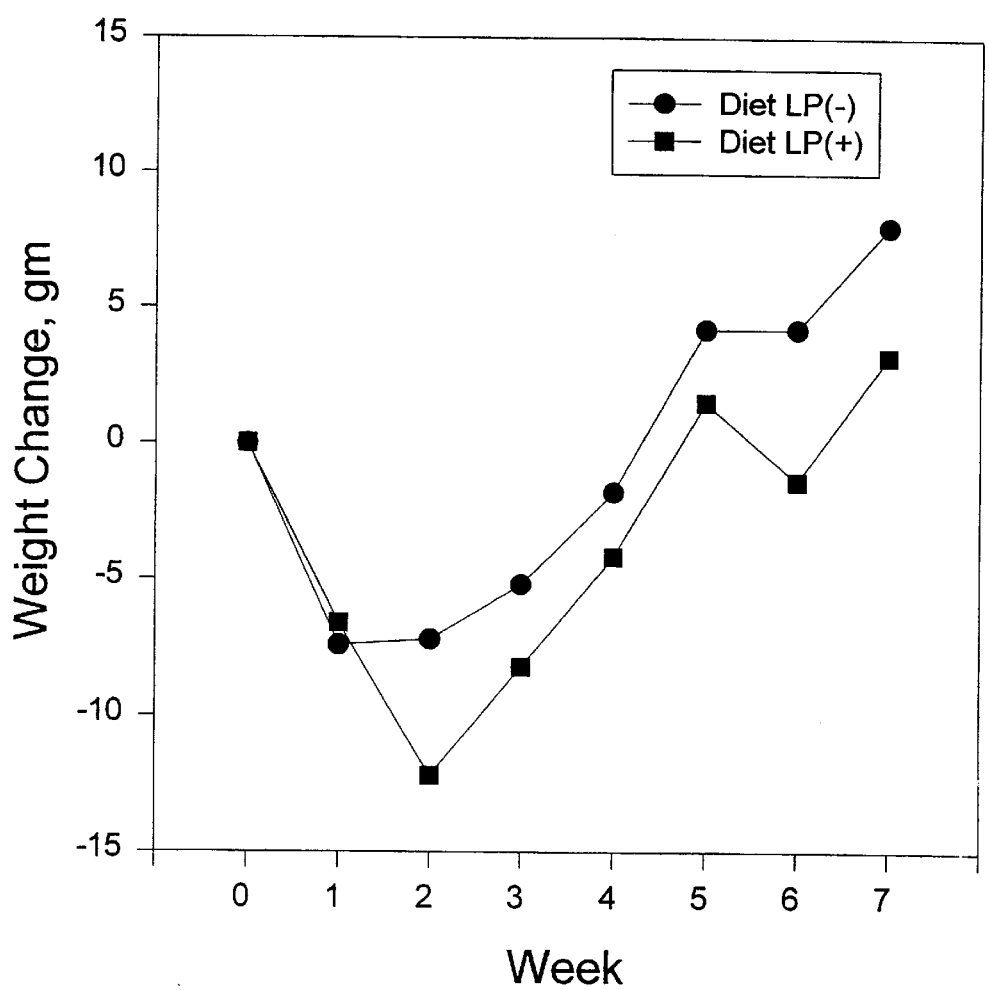
Fig. 6 Cumulative Body Weight Change of Obese Rats Fed ad lib Diets LP(-) or LP(+).

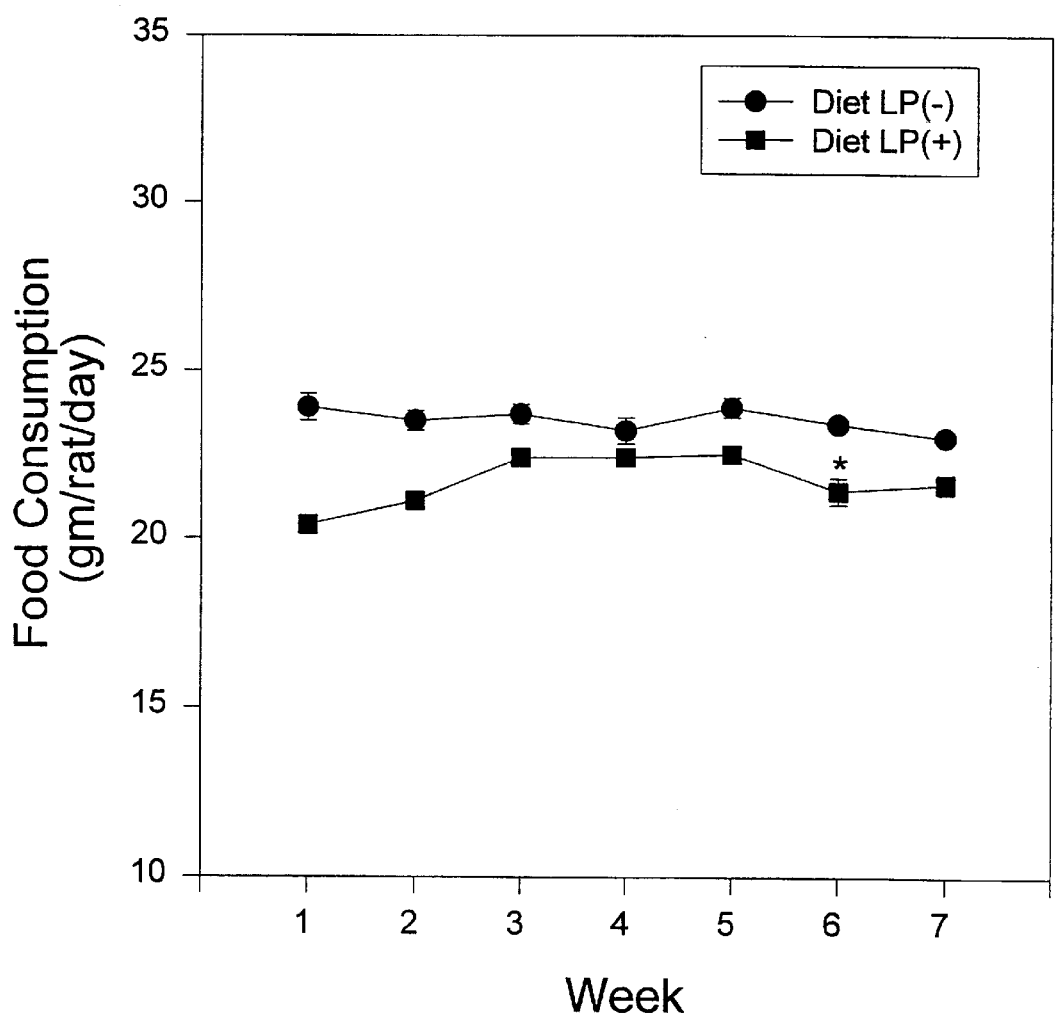
Fig. 7 Weekly Food Consumption of Obese Rats Fed ad lib Diets LP(-) or LP(+).

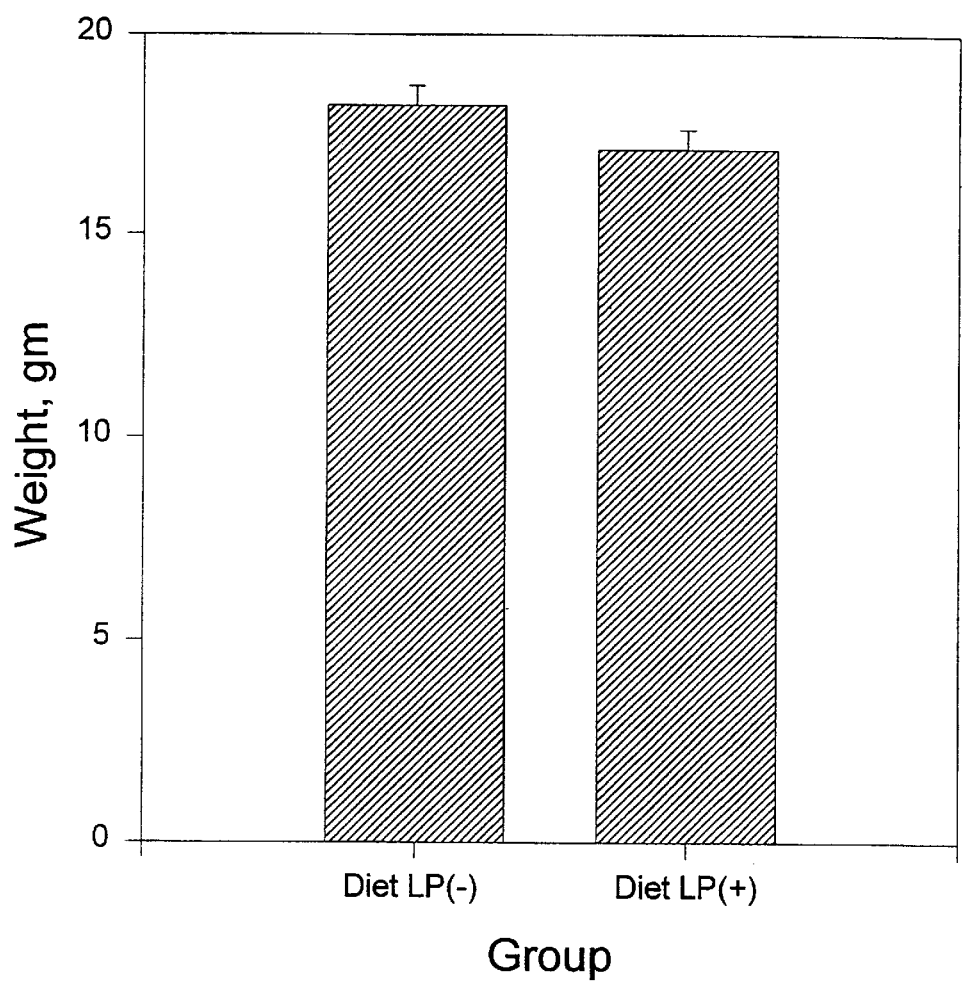
Fig. 8 Retroperitoneal Fat Pad Weight of Obese Rats Fed ad lib Diet LP(-) or Diet LP(+).

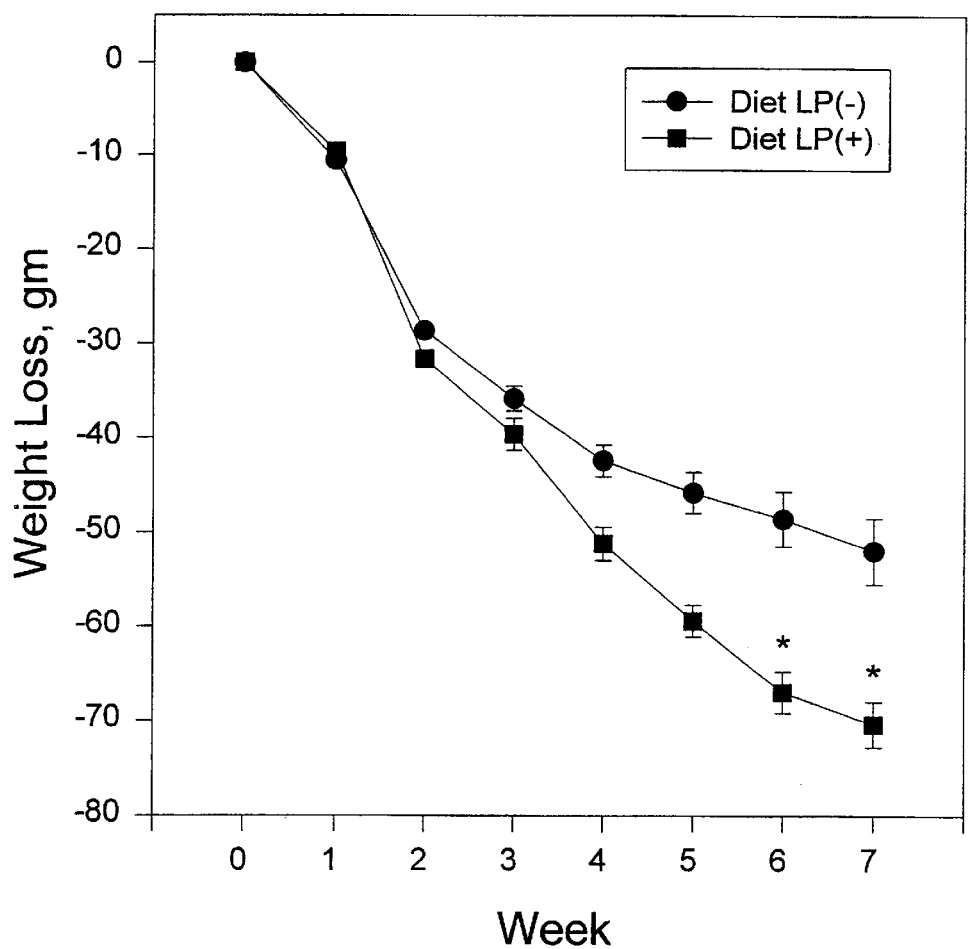
Fig. 9 Cumulative Weight Loss of Obese Rats Food Restricted with Diets LP(-) or LP(+).

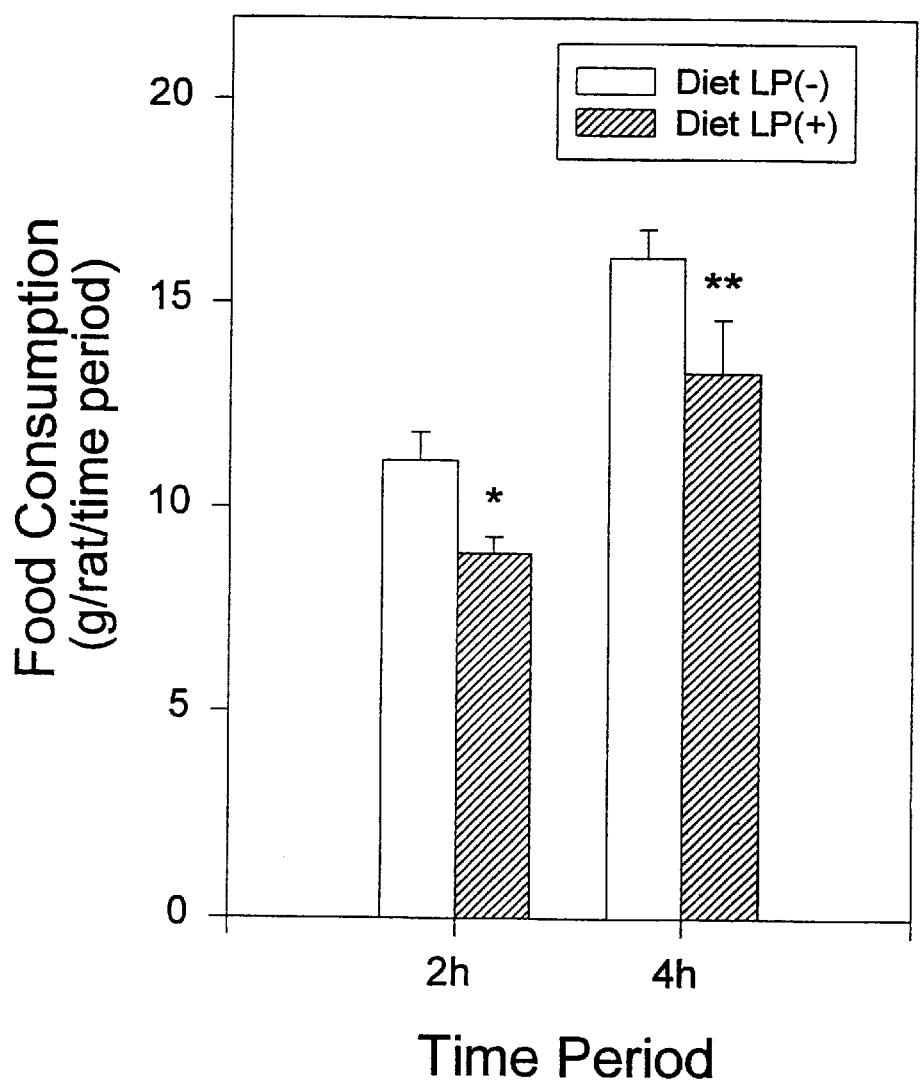
Fig. 10 Mean 2h and 4h Food Consumption for Obese Rats Fed Diets LP(-) or LP(+).

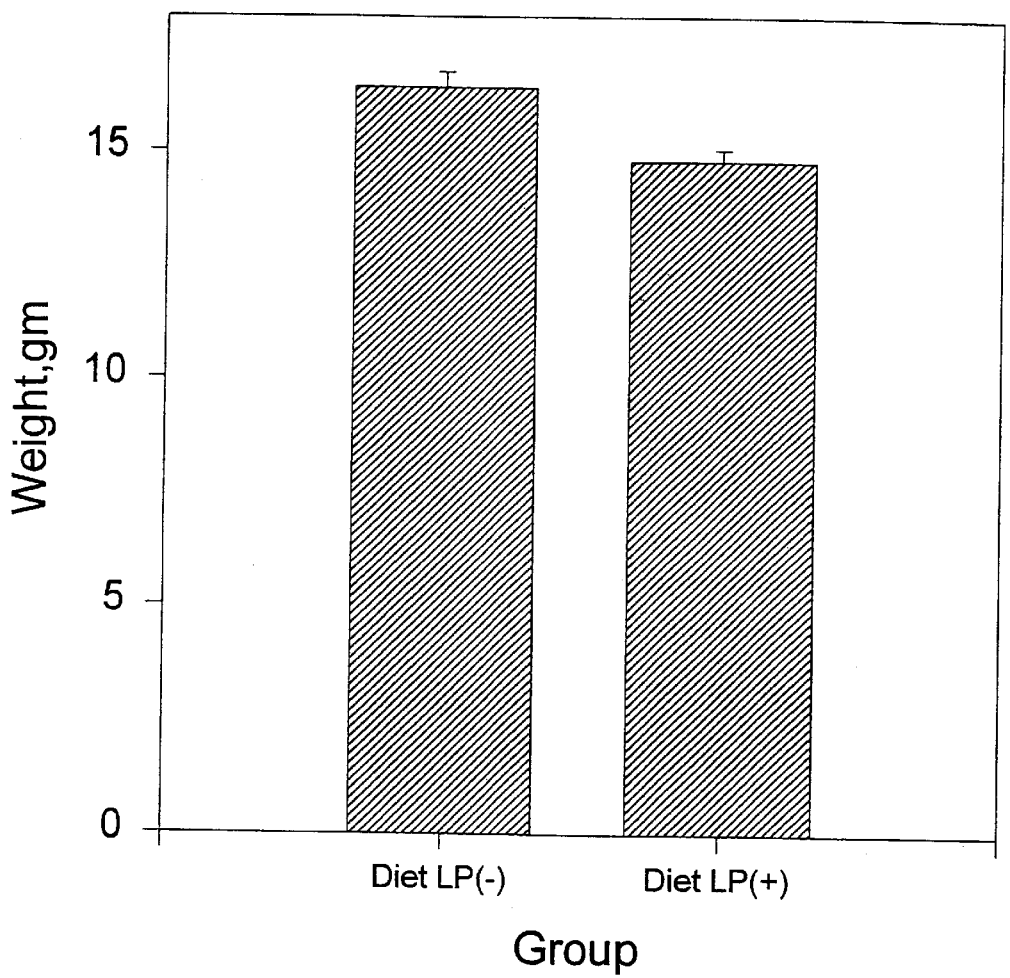
Fig. 11 Retroperitoneal Fat Pad Weight of Obese Rats Food Restricted with Diet LP(-) or Diet LP(+).

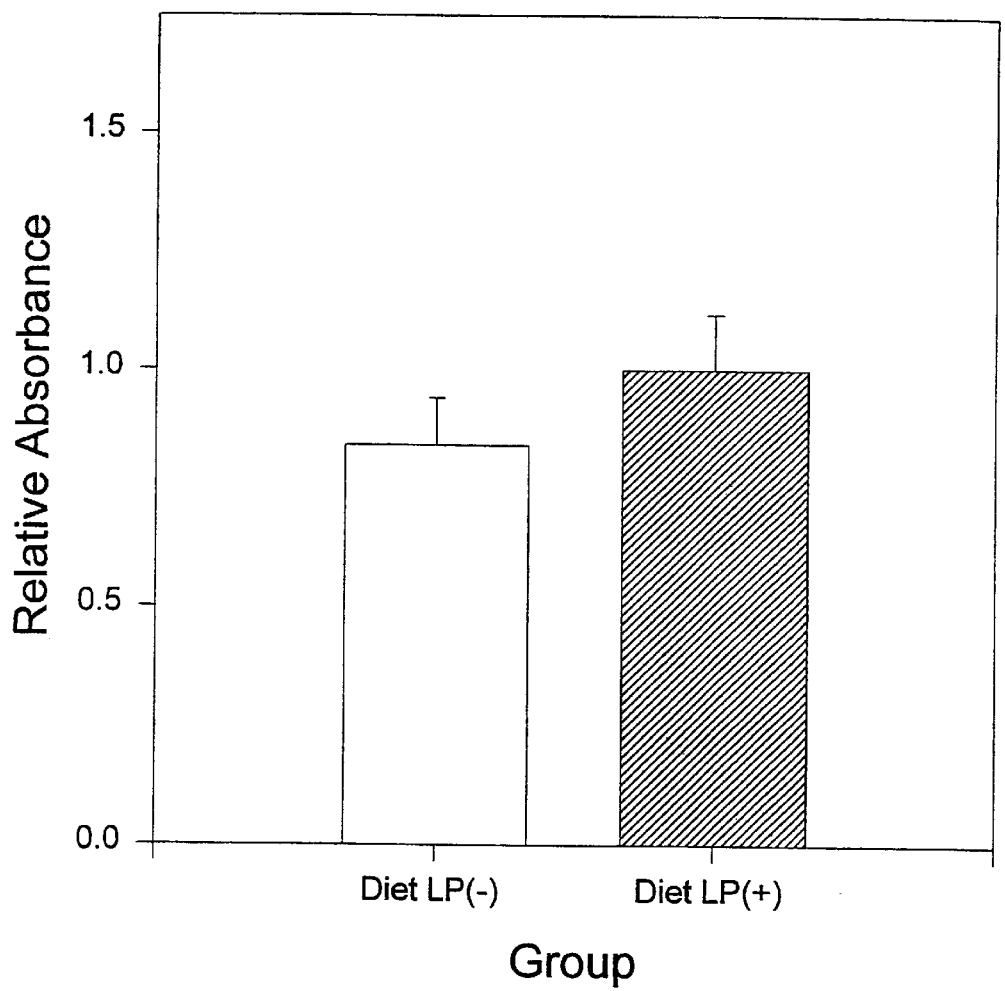
Fig. 12 Hypothalamic PreproGRF mRNA in Obese Rats Food Restricted Diets LP(-) or LP(+).

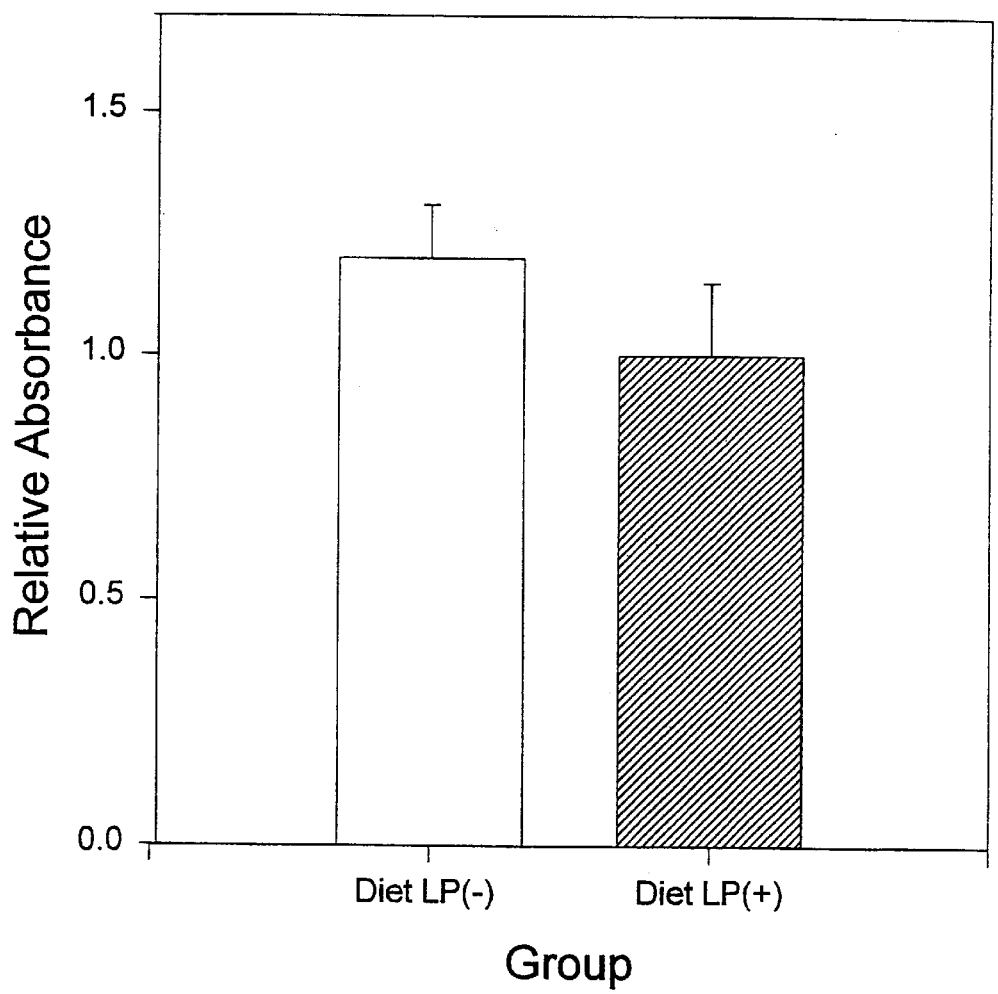
Fig. 13 Hypothalamic PreproNPY mRNA in Obese Rats Food Restricted Diets LP(-) or LP(+).

METHOD OF REGULATING APPETITE AND METABOLISM

This work was sponsored, in part, by the National Science Foundation, Grant BNS 9007573. The U.S. Government may have certain rights in the invention.

FIELD OF THE INVENTION

The present invention relates to weight control in animals by regulating both appetite and metabolism. More particularly, the present invention relates to weight control in humans and other animals using a diet with reduced calories, reduced or no fat, and a controlled amount of protein in combination with supplemental dietary amino acids to control appetite and modulate the effects of an altered metabolism during dieting.

BACKGROUND OF THE INVENTION

Obesity is a recognized health problem which is associated with cardiovascular disease, diabetes and certain forms of cancer. It is well established that although disciplined dieting may result in weight loss, such weight loss is rarely long lasting due to two distinctive effects which are associated with dieting. These effects are a notable increase in hunger, or drive to eat, and a notable decrease in the basal metabolic rate of the dieting individual. Thus, a frequent consequence of dieting with low caloric intake is an increase in weight gain or rebound effect in weight gain to or beyond the original pre-diet weight due to increased hunger and a concomitant reduction in basal metabolic rate following termination of the low caloric diet.

Obesity most commonly arises as a result of the imbalance of caloric intake (eating) vs. caloric expenditure. However, the propensity to become obese may be affected by certain genes and, in addition, certain metabolic disorders have a direct effect on weight gain, for example, growth hormone deficiency or hypothyroidism. Regardless of the underlying physiological cause of obesity, appetite regulation is a key factor in controlling weight gain and maintenance of body weight.

Recent scientific advances in cellular and molecular endocrinology, neurobiology, and physiology have greatly expanded the understanding of the complex hormonal and neural pathways regulating body weight and appetite. It is now clear that neural and hormonal systems interact at virtually every step in feeding satiety and metabolic control. Central to this new understanding has been the recognition of the roles subserved by key neural systems operating within the brain, specifically within the hypothalamus.

Of the many systems acting within the hypothalamus to regulate appetite and metabolism is neuropeptide Y (NPY) which is now recognized to play a pivotal role. NPY is a 36 amino acid peptide secreted by hypothalamic neurons and is the most potent (on a molar basis) naturally occurring substance yet discovered that stimulates appetite. NPY belongs to a family of neuroendocrine peptides including pancreatic polypeptide and peptide YY. Interestingly, both the amino acid sequence of NPY and the location of NPY-expressing neurons within the brain have been highly evolutionarily conserved, evidencing that the physiological role of hypothalamic NPY is universal among vertebrates (D. Larhammar, "Evolution of neuropeptide Y, peptide YY and pancreatic polypeptide," *Regulatory Peptides*, 62:1–11 (1996)). NPY, when administered into the brain, causes a long-lasting increase of food intake and when given chronically, results in development of obesity reviewed in White, "Neuropeptide Y: a central regulator of energy homeostasis," *Regulatory Peptides*, 49:93–107 (1993). Similarly, high levels of NPY are observed specifically in the hypothalamus of obese animals (Sanacora et al., "Increased hypothalamic content of preproneuropeptide Y messenger ribonucleic acid in genetically obese Zucker rats and its regulation by food deprivation," *Endocrinology*, 127:730–737 (1990); Sanacora et al., "Developmental aspect of differences in hypothalamic preproneuropeptide Y messenger ribonucleic acid content in lean and genetically obese Zucker rats," *J Neuroendocrinol.*, 4:353–357 (1990)); and food deprived or food restricted animals (White and Kershaw, "Increased hypothalamic neuropeptide Y expression following food deprivation," *Molec. Cell. Neurosci.*, 1:41–48 (1990); Sahu, et al. "Hypothalamic preproNPY mRNA levels in rats subjected to a scheduled feeding regimen," *Molecular Brain Research*, 15:15–18 (1992)). As these studies predict, reduction in hypothalamic NPY levels is associated with reduced food intake.

In summary, secretion of NPY from neurons within the hypothalamus stimulates feeding and chronically high levels of NPY expression result in hyperphagia and obesity. The ability to reduce high levels of NPY results in the diminution of the drive to eat. NPY gene regulation and physiology are reviewed in Berelowitz et al., "Regulation of hypothalamic neuropeptide expression by peripheral metabolism," TEM 3:127–133 (1992), the disclosure of which is herein incorporated by reference.

Growth hormone releasing factor (GRF), also called growth hormone releasing hormone (GHRH), is a 44 amino acid peptide of the glucagon-VIP-PHI family and is present in high concentration in the hypothalamus, particularly in the arcuate nucleus and medium eminence. GRF is the primary stimulatory factor controlling synthesis and secretion of pituitary growth hormone (GH), a critical regulatory hormone of metabolic homeostasis controlling breakdown of fat (lipolysis) and synthesis of protein. Thus a normal level of GRF is required for appropriate levels of GH to maintain muscle mass while promoting lipolysis (Berelowitz et al. (1992), supra).

The relationship between hypothalamic levels of GRF and food deprivation is the opposite of that observed with NPY. Specifically, levels of GRF are reduced in the hypothalamus following food deprivation (White et al., "Localization of prepro-growth hormone releasing factor mRNA in rat brain and regulation of its content by food deprivation and experimental diabetes," *Molec. Cell. Neurosci.*, 1:183–192 (1990); Bruno et al., "Influence of food deprivation in the rat on hypothalamic expression of growth hormone-releasing factor and somatostatin," *Endocrinology*, 127:2111–2116 (1990)). Moreover, expression of GRF is also reduced in animals made obese by ingestion of a high-fat diet compared to GRF expression in normal non-obese animals fed a normal diet (Berelowitz et al. (1992), supra).

When an individual diets, the body compensates with a reduced metabolic rate based on the lower caloric intake. In essence, the body down-regulates the requirement for food, thereby subsisting on less food. As dieting continues, the threshold for caloric intake is reduced. When dieting has ended, the individual typically gains weight while eating a normal diet because of the lowered caloric intake threshold and lower-basal metabolic rate (NIH Technology Assessment Conference Panel, "Methods for voluntary weight loss and control," *Ann. Intern. Med.*, 116:942–949 (1992); Wadden, "Treatment of Obesity by moderate and severe caloric restriction," *Ann. Intern. Med.*, 119:688–693 (1993)).

The reduction in GRF levels in food-deprived rats has been attributed to a lack of dietary protein (Bruno et al., "Regulation of rat hypothalamic prepro-growth hormone-releasing factor messenger ribonucleic acid by dietary protein," *Endocrinology*, 129:1226–1232 (1991)), which reduction is reversed in part upon supplementation of the diet with the amino acid histidine (Bruno et al., "Regulation of hypothalamic preprogrowth hormone-releasing factor messenger ribonucleic acid expression in food-deprived rats: A role for histaminergic neurotransmission," Endocrinology, 133:1377–1381 (1993)).

Latham and Blundell, "Evidence for the effect of tryptophan on the pattern of food consumption in free feeding and food deprived rats," *Life Sciences*, 24:1971–1978 (1979), report that intravenous administration of L-tryptophan to rats reduces their overall intake of a normal calorie diet within about 4 hours post-administration of the compound. Thereafter, tryptophan appeared to have little effect on food intake in the rats.

There are available a vast array of diets which purport to be effective in reducing weight in animals, particularly humans. However, while these diets may have resulted in some success regarding weight loss, many of them do not promote long term loss of weight since, unless they are accompanied by ingestion of chemical appetite suppressants, they do not effectively reduce the drive to eat.

The present invention satisfies a long felt need in the art of weight reduction by providing a diet which is specifically designed to concomitantly reduce caloric intake and regulate either, and preferably both the drive to eat and the metabolic effects of dieting, thereby promoting and enhancing long-term weight loss.

BRIEF SUMMARY OF THE INVENTION

The invention relates to methods and compositions capable of modulating appetite and reducing obesity in an animal, preferably a human, which methods and compositions involve modulation of synthesis and secretion of neuropeptide Y, as evidenced, for example, by the level of mRNA coding for preproNPY ("preproNPY mRNA") and modulation of synthesis and secretion of growth hormone releasing factor as evidenced, for example, by the level of mRNA coding for preproGRF("preproGRF mRNA"), to levels consistent with levels in a like, normal, nonobese animal.

Accordingly, one aspect of the invention involves a method of reducing an animal's drive to eat comprising administering to the animal a diet comprising a lower amount of calories and protein than in a preadministation diet prior to administering the lower calorie, lower protein diet, and supplementing the diet with an appetite-reducing amount of tryptophan sufficient to reduce the animal's level of neuropeptide Y compared to a pre-administration level of neuropeptide Y.

Another aspect of the invention relates to a method of weight control in an animal comprising administering to the animal a diet comprising a lower amount of calories and protein than in a preadministation diet prior to administering the lower calorie, lower protein diet, and supplementing the diet with an appetite-reducing amount of tryptophan sufficient to reduce the animal's level of neuropeptide Y compared to a pre-administration level of neuropeptide Y.

Another aspect of the invention relates to a method of stabilizing an animal's metabolic rate comprising administering to the animal a diet comprising a lower amount of calories and protein than in a preadministation diet prior to administering the lower calorie, lower protein diet, and supplementing the diet with an amount of histidine sufficient to elicit an increase of a metabolic rate-stabilizing amount of growth hormone releasing factor in the animal to a level compared to a pre-administration level of growth hormone releasing factor.

Still another aspect of this invention relates to a method of weight control in an animal comprising administering to the animal a diet comprising a lower amount of calories and protein than in a preadministation diet prior to administering the lower calorie, lower protein diet, and supplementing the diet with an amount of histidine sufficient to elicit an increase of a metabolic rate-stabilizing amount of growth hormone releasing factor in the animal compared to a pre-administration level of growth hormone releasing factor.

Yet another aspect of this invention relates to a method of reducing an animal's drive to eat and increasing the animal's metabolic rate comprising administering to the animal a diet comprising a lower amount of calories and protein than in a preadministation diet prior to administering the lower calorie, lower protein diet, and supplementing the diet with an appetite-reducing amount of tryptophan sufficient to reduce the animal's level of neuropeptide Y compared to a pre-administration level of neuropeptide Y and with an amount of histidine sufficient to elicit an increase of a metabolic rate-stabilizing amount of growth hormone releasing factor in the animal compared to a pre-administration level of growth hormone releasing factor.

Another aspect of the present invention relates to a method of weight control in an animal comprising administering to the animal a diet comprising a lower amount of calories and protein than in a preadministation diet prior to administering the lower calorie, lower protein diet, and supplementing the diet with an appetite-reducing amount of tryptophan sufficient to reduce the animal's level of neuropeptide Y compared to a pre-administration level of neuropeptide Y and with an amount of histidine sufficient to elicit an increase of a metabolic rate-stabilizing amount of growth hormone releasing factor in the animal compared to a pre-administration level of growth hormone releasing factor.

Still another aspect of the present invention relates to a method of controlling secretion of neuropeptide Y in an animal comprising administering to the animal, at a controlled release rate, a neuropeptide Y-modulating amount of tryptophan sufficient to elicit a reduced level of neuropeptide Y over a sustained period of at least about 4 hours.

Yet another aspect of this invention is a method of controlling the secretion of neuropeptide Y and growth hormone releasing factor in an animal comprising administrating to the animal, at a controlled release rate, a neuropeptide Y-modulating amount tryptophan and a growth hormone releasing factor-modulating amount of histidine sufficient to elicit a respective reduced level of neuropeptide Y and an increased level of growth hormone releasing factor, compared to pre-administration levels of neuropeptide Y and growth hormone releasing factor, over a sustained period of at least about 4 hours.

In addition to the foregoing methods, the present invention is directed to compositions for controlling weight, especially in humans. Accordingly, this invention also relates to a human food composition wherein the composition comprises a daily diet of less than about 2,400 calories, about 10 grams (g) to about 540 g of protein and about 5 mg to about 125 mg of tryptophan per g of protein.

This invention also relates to a human food composition wherein the composition comprises a daily diet of less than about 2,400 calories, about 10 g to about 36 g of protein and about 10 mg to about 270 mg of histidine per g of protein.

This invention further relates to a human food composition wherein the composition comprises a daily diet of less than about 2,400 calories, about 10 g to about 36 g of protein, about 5 mg to about 125 mg of tryptophan per g of protein and about 10 mg to about 270 mg of histidine per g of protein.

BRIEF DESCRIPTION OF THE DRAWINGS

The accompanying drawings illustrate various data in graphical format to better explain the invention by way of reference to specific, exemplary, non-limiting, experimental studies.

FIG. 1 is a histogram of relative mean densitometric values (density) from nuclease protection analysis in which the levels of preproNPY mRNA were measured in hypothalamic extracts from sacrificed rats over indicated time periods of food deprivation compared to control rats which were freely fed and where the control was arbitrarily set to equal 1.0. Fed, freely fed (ad libitum) controls; FD, food-deprived; *, significantly different from control values by one-way ANOVA, $p<0.05$, followed by Fischers least significant difference (LSD) test.

FIG. 2 is a histogram of the relative density of hypothalamic preproNPY mRNA levels during food deprivation and during refeeding of rats during the indicated time periods. Abbreviations and symbols are the same as those used in FIG. 1, and RF, refed after food deprivation and measured the indicated hours after refeeding.

FIG. 3 is a histogram illustrating the relative density of hypothalamic preproNPY mRNA with respect to selective nutrient refeeding following food deprivation compared to freely fed control, food deprived and normal refed rats. Abbreviations and symbols are the same as those used in FIGS. 1 and 2, and NRF, normal refeed; FFRF, fat-free refed; PFRF, protein-free refed; CFRF, carbohydrate-free refed.

FIG. 4 is a histogram illustrating the relative density of hypothalamic preproNPY mRNA with respect to graded percentages of protein refeeding following food deprivation compared to freely fed control rats and food-deprived rats. Abbreviations and symbols are the same as those used in FIGS. 1–3, and % PRF, % protein refed.

FIG. 5 is a histogram showing the relative density of hypothalamic preproNPY mRNA with respect to control, freely fed and food-deprived rats comparing different types of refeed diets. Abbreviations and symbols are the same as those used in FIGS. 1–4, and Tyr, refed protein-free food supplemented with tyrosine; Trp, refed protein-free food supplemented with tryptophan; GA, refed protein-free food supplemented with glutamic acid; His, refed protein-free food supplemented with histidine.

FIG. 6 is a graph illustrating the change in cumulative body weight of obese rats freely fed with diets LP(−) or LP(+) over a 7-week period. LP(−), low protein diet supplemented with control amino acids (phenylalanine and valine); LP(+), low protein diet supplemented with tryptophan, histidine and arginine.

FIG. 7 is a graph illustrating weekly food consumption of obese rats fed freely diets LP(−) or LP(+) over a 7-week period. *, statistically significant $p<0.05$ versus the corresponding LP(−) time point.

FIG. 8 is a graph illustrating the retroperitoneal fat pad weight of obese rats fed freely diet LP(−) or LP(+).

FIG. 9 is a graph illustrating the cumulative weekly weight loss of obese rats fed restricted diets LP(−) or LP(+). *, statistically significant $p<0.05$ versus the corresponding LP(−) time point.

FIG. 10 is a graph showing mean food consumption for obese rats fed diets LP(−) or LP(+), where food intake represents the mean±SEM of total food consumed by 2 hours and 4 hours following lights out, measured over a 14-day period. *, statistically significant with $p<0.05$ compared to diet LP(−) 2-hour food consumption; **, statistically significant $p<0.001$ compared to diet LP(−) 4-hour food consumption.

FIG. 11 is a graph illustrating the retroperitoneal fat pad weight of obese rats fed with restricted diets LP(−) or LP(+).

FIG. 12 is a graph illustrating the relative absorbance of hypothalamic preproGRF mRNA levels in obese rats fed different food-restricted diets.

FIG. 13 is a graph illustrating the relative absorbance of hypothalamic preproNPY mRNA levels in obese rats fed restricted diets LP(−) or LP(+).

DETAILED DESCRIPTION OF THE INVENTION

The present invention relates to methods and compositions for controlling weight in an animal, and particularly in humans. As used herein, the term "controlling weight" and its grammatical equivalents mean reducing obesity by losing weight or by not gaining weight.

The inventors have discovered that administration to an animal of a diet, preferably a low calorie, low or no fat and low protein diet supplemented with the amino acid L-tryptophan, reduces the synthesis and secretion of hypothalamic NPY, and reduces appetite. Reducing appetite is likely to result in controlling weight. Administration to an animal of a diet, preferably a low calorie, low or no fat and low or no protein diet supplemented with the amino acid L-histidine, induces the synthesis and secretion of hypothalmic GRF, which modulates metabolism during dieting, such that a lower caloric threshold or set point is not established. This helps prevent weight gain when dieting is concluded, and thus controls weight. According to the present invention, controlling weight is enhanced by administering a diet including sufficient amounts of both tryptophan, to modulate (and preferably reduce) the synthesis and secretion of NPY to effectively reduce appetite, and histidine, to modulate (and preferably increase) the synthesis and secretion of GRF to effectively regulate metabolism.

In particular, the inventors have discovered that administration of tryptophan and histidine to an animal in a diet which is a low calorie diet having a defined amount of protein has the following effects: The appetite of the animal is reduced; the animal loses weight; the percent body fat of the animal is reduced; and, the level of NPY is reduced and the level of GRF is increased compared with NPY and GRF levels prior to the administration of tryptophan and histidine.

Thus, according to the present invention, supplementation of a low protein diet with tryptophan and histidine results in a reduction in the drive to eat in an animal and modulation of metabolism as described above. The effects of tryptophan and histidine on appetite control are most marked when the animal is fed a diet comprising a lower than normal protein content and which is supplemented by one or preferably both, of tryptophan or histidine.

The methods of the invention are most useful in controlling weight, in obese humans or animals, including pets and other animals such as dogs, cats, horses, pigs, cows, and sheep. Obesity in humans or animals is generally characterized by weight and body mass particularly of fat tissue above currently accepted standards. Obesity in a human is defined as a condition where the individual has a Body Mass Index ("BMI"), sometimes called Quetelet's Index, above currently accepted standards. BMI is calculated by dividing weight (in kg) by height$^2$ (in meters$^2$). The current standards for both men and women accepted as "normal" are a BMI of 20–24.9 kg/m$^2$. Grade I obesity corresponds to a BMI of 25–29.9 kg/m$^2$; Grade II obesity corresponds to a BMI of 30–40 kg/m$^2$; and Grade III obesity corresponds to a BMI greater than 40 kg/m$^2$. (E. Jéquier, "Energy, obesity, and body weight standards," *Am. J Clin. Nutr.*, 45:1035–47 (1987)). Ideal body weight will vary among species and individuals based on height, body build, bone structure, and sex.

A normal daily diet in humans generally comprises the following: about 2,800 to significantly more calories, comprising about 12 g to about 45 g of protein, about 120 g to about 610 g of carbohydrate, and about 11 g to about 90 g of fat. A low calorie diet would be no more than about 85%, and preferably no more than about 70%, of the above.

In animals, the caloric requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake.

To effect weight loss in an obese individual, or even in an individual who is not obese but who desires to lose or otherwise control weight, a diet may be administered to the individual which results in modulation of NPY and/or GRF levels in the individual sufficient to reduce appetite and avoid setting a significantly lower metabolic threshold which would tend to lead to weight gain upon concluding the diet.

The diet comprises a low calorie, low protein diet which is supplemented with an amount of tryptophan sufficient to lower levels of NPY in the individual to normal non-obese levels and thereby control the individual's desire to eat. In humans, although the amounts may vary from individual to individual, suitable amounts of tryptophan that are capable of reducing the levels of NPY a minimum of 15% below baseline value, are estimated to be about 5 mg to about 125 mg per g protein. The preferred and more preferred amounts of tryptophan that are required to decrease the levels of NPY to a minimum of 15% below baseline values are 6 mg/g protein to about 61 mg/g protein and about 8 mg/g protein to about 31 mg/g protein, respectively.

The low calorie, low protein diet may be further supplemented with an amount of histidine sufficient to increase the levels of GRF in the individual and thereby restore depressed serum growth hormone levels such that the basal metabolic rate is equal to or greater than the predict basal metabolic rate. In adult humans, GH acts as a principal metabolic regulatory hormone, promoting lipolysis and inhibiting protein breakdown. Release of GH is controlled by hypothalamic GRF and increasing GRF levels correlates with a rise in plasma GH levels. In obese humans, low plasma GH levels are associated with a reduced metabolic rate, and with increased fat deposition and protein breakdown (C. Dieguez, M. D. Page and M. F. Scanlon, "Growth hormone neuroregulation and its alterations in disease states," *Clinical Endocrinology*, 28:109–143 (1988)). Thus, the desired target metabolic rate is where the body burns fat in preference to lean body tissue, and may be determined by comparing the amount of fatty tissue to lean body tissue, ascertained by measuring total body weight and fat content at the beginning and end of the dietary period. Based on animal data (Bruno et al. (1993), supra), suitable amounts of histidine that are capable of elevating the levels of GRF to a minimum of 15% above baseline values in obese humans are estimated to be about 10 mg/g protein to about 270 mg/g protein. The preferred and more preferred ranges of histidine are about 15 mg/g protein to about 135 mg/g protein and about 17 mg/g protein to 68 mg/g protein, respectively.

It is believed that low levels of GRF contribute to low levels of plasma GH which correlates with a lower catabolism of fat tissue to lean tissue, hereinafter "fat/lean tissue catabolism". Therefore, raising plasma GH levels desirably increases fat/lean tissue catabolism. Raising hypothalamic GRF levels correlates with raising plasma GH levels.

The present invention includes a method of controlling the secretion of NPY and GRF in an animal, and preferably a human, comprising administering to the animal or human, at a controlled release rate, an NPY-modulating amount of tryptophan and a GRF-modulating amount of histidine sufficient to elicit a respective reduced level of NPY and an increased level of GRF, compared to pre-administration levels of NPY and GRF, over a sustained period of at least about 4 hours. It is preferred that the sustained period be at least 8 hours, and more preferred over at least 12 hours. The amounts of tryptophan and histidine can be adjusted based on observing the eating behavior of the animal, or after eliciting feedback concerning hunger, appetite and amount of food consumed, from humans. Various sustained time-release forms of tryptophan and histidine can be formulated by one of ordinary skill in the art based on the disclosure of the present invention in view of the many types of well-known time-release compositions that have been and are available. Therefore, further details concerning this embodiment of the present invention need not be disclosed herein.

According to the invention, the individual desiring to lose weight preferably is administered a low calorie, low protein diet, supplemented with tryptophan and histidine in place of a normal diet. Typically, the low calorie, low protein supplemented diet of the invention is administered about three times (i.e., given in three meals) during the course of a day, but the frequency of administration or consumption is not as important as total daily administration or consumption. Thus, the total amount to be ingested per day may be administered in one serving or in many more than one serving per day, depending on the eating habits of the individual or animal. Likewise, specific calorie requirements may need to be adjusted on an individual basis, i.e., sex body build, activity, etc.

The present invention includes a human food composition wherein the composition comprises a daily diet of less than about 2,400 calories, about 10 g to about 540 g of protein and at least one of (a) about 5 mg to about 125 mg of tryptophan per g of protein and (b) about 10 mg to about 270 mg of histidine per g of protein.

A preferred human food composition of this invention comprises a daily diet of about 800 to about 1,200 calories, about 10 g to about 270 g of protein and at least one of (a) about 6 mg to about 61 mg of tryptophan per g of protein and (b) about 15 mg to about 135 mg of histidine per g of protein.

A more preferred human food composition according to this invention comprises a daily diet of less than about 800 calories, about 10 g to about 180 g of protein and at least one of (a) about 8 mg to about 31 mg of tryptophan per g of protein and (b) about 17 mg to about 68 mg of histidine per g of protein.

Another preferred human food composition of this invention comprises a daily diet of less than about 2,400 calories, about 10 g to about 540 g of protein, about 60 g to about 540 g of carbohydrate, about 2 g to about 240 g of fat, and at least one of (a) about 5 mg to about 125 mg of tryptophan per g of protein and (b) about 10 mg to about 270 mg of histidine per g of protein.

Still another preferred human food composition according to this invention comprises a daily diet of about 800 to about 1,200 calories, about 10 g to about 270 g of protein, about 30 g to about 270 g of carbohydrate, about 1 g to about 120 g of fat, and at least one of (a) about 6 mg to about 61 mg of tryptophan per g of protein and (b) about 15 mg to about 135 mg of histidine per g of protein.

A still more preferred human food composition of this invention comprises a daily diet of less than about 800 calories, about 10 g to about 180 g of protein, about 20 g to about 180 g of carbohydrate, about 0.5 g to about 80 g of fat, and at least one of (a) about 8 mg to about 31 mg of tryptophan per g of protein and (b) about 17 mg to about 68 mg of histidine per g of protein.

In each of the foregoing human food compositions, it is preferred that the respectively indicated amounts of tryptophan and histidine are both present, to obtain the appetite reduction and basal metabolic regulatory function of both to better enhance the desired weight control effect of the present invention.

While the rate of weight loss in an individual may vary depending on many psychological and physical factors, including the actual genesis of the obese condition, it is anticipated that an individual who adheres to the diet regimen will experience measurable weight loss within about 2 weeks and beyond.

To assess the effects of the practice of the methods of the invention on obesity in a human, weight, body fat and appetite are measured in each individual on the diet. Human weight may be assessed using a standard, preferably calibrated scale at frequent, preferably uniform intervals ranging from once daily to every several days to weekly or even less or more frequently.

Percent body fat in a human may be measured by standard techniques, such as those described in Katch and McArdle: *Nutrition, Weight Control, and Exercise*, 3rd ed., Leah Ferbiger, Philadelphia (1988).

Several commonly used procedures to assess percent body fat are:

1) Hydrostatic weighing (also referred to as underwater weighing): This procedure computes an individual's body volume as the difference between body weight measured in air and weight measured during water submersion, i.e., body volume is equal to the loss of weight in water (with the appropriate temperature correction for the water's density). The individuals body density is then calculated as body weight divided by body volume. The relative percent of fat in the human body can then be estimated with a simple equation that incorporates body density:

Percent fat=495/density−450.

This equation was derived from the theoretical premise that the densities of fat and fat-free tissues remain relatively constant even with large variations in total body fat.

2) Body Mass Index ("BMI"), or the Quetelet's index, described above.

3) Measurement of subcutaneous fat by the fat fold technique: In this technique, a pincer-type caliper is used to measure subcutaneous fat by determining skin fold thickness at representative sites on the body. These skin fold measurements are then used to compute body fat by either adding the scores from the various measurements and using this value as an indication of the relative degree of fatness among individuals or by using the measurements in mathematical equations that have been developed to predict percent body fat.

4) Ultrasound: In this technique, an ultrasound meter is used to measure the distance between the skin and fat-muscle layer, and between the fat-muscle layer and bone. The high frequency sound waves emitted by the meter pass through adipose tissue until they reach the muscle layer where the waves are reflected from the fat muscle interface to produce an echo that travels back to the meter where it is converted to a distance score. The distance the waves travel indicates fat thickness. Measurements are performed at various sites of the body and used in mathematical formulas to calculate percent body fat.

5) Bioelectrical impedance test: In this technique, electrodes are attached to one hand and one foot of an individual and a radio frequency pulse is run through the body to measure its water content which is used as a guide to body fat.

Further, appetite in a human is assessed by measuring the amount of food ingested and by assessing the individual's desire to eat. Appetite (i.e., hunger) is typically assessed with a short questionnaire given to individuals on a random basis several times a week. Typically, subjects rate their hunger, preoccupation with food, and desire to eat greater quantities and different types of food by answering the questions using analogue scales ranging from 1, not at all, to 5, extremely.

The invention will now be described with reference to the specific examples provided below, but should in no way be construed as being limited in any way solely to these examples. As used herein, all percentages of components of compositions are percent by weight of the overall composition, unless it is clearly otherwise from the context in which the percentages are used.

EXAMPLE 1

The data presented in this section are derived from early experiments designed to understand how peripheral metabolic status modulates NPY gene expression in the hypothalamus. Experimental evidence accumulated from several laboratories has directly implicated hypothalamic NPY in regulation of feeding. The mechanisms of appetite and body-weight regulation by peripheral signals are highly complex but such regulation must involve interactions between peripheral metabolic status and the brain. Since the hypothalamus has long been recognized as central in recognition of peripheral nutrient and metabolic signals and in regulation of hunger and satiety responses, it was considered a logical site to focus research aimed at understanding interactions between and regulation of the periphery and central nervous system.

Food deprivation was the experimental paradigm utilized for these studies, a state of aberrant metabolic homeostasis. The rational for using this model was as follows:

Since NPY is a potent regulator of appetite, the expression of NPY should be altered in an experimental system of aberrant metabolism, i.e., food deprivation. Thus, our predictions were that food-deprived animals would have increased NPY expression (continuous stimulation of the drive to eat) compared to fed controls and that refeeding would restore NPY levels to that seen in normal satiated animals. Moreover, the food deprivation model was used to permit a detailed evaluation of potential metabolic signals, i.e., nutrients (fat, protein and carbohydrates) that act as modulators of NPY expression.

Animals and Experimental Procedure

Male Sprague-Dawley rats weighing 200–250 g were housed in groups of two under constant temperature (22° C.) and a 12 h light, 12 h dark cycle (lights on at (07:00 h) and were provided free access to rat chow (Ralston-Purina, St. Louis, Mo.) and tap water. Animals were adapted for 5–7 days before all experimental procedures.

Food Deprivation Time Course.

To determine the time course of changes in hypothalamic preproNPY mRNA levels occurring as a result of nutrient deprivation, animals were either allowed free access to food or were killed after 24, 48, or 72 h of food deprivation (n=6/group). All animals had free access to water, and body weights were recorded before food deprivation and at death. The results are shown in FIG. 1 and discussed below.

Refeeding after 72 h offood deprivation.

The effect of refeeding on increased hypothalamic pre-proNPY mRNA content after 72 h food deprivation was determined in groups of rats allowed free access to food or food-deprived rats for 72 h then permitted to refeed ad libitum for 24, 48, or 72 h (n=6/group). All groups had free access to water and were weighed before and after food deprivation and again after refeeding. The results are shown in FIG. 2 and discussed below.

Select Nutrient Refeeding.

For these experiments, animals were adapted for 3–5 days to the facility at which time they were fed an American Institute of Nutrition (AIN) 76A Semipurified Diet; hereafter referred to as a "normal" diet, ad libitum for 3 days before the start of all experiments. The normal diet and all other isocaloric test diets were purchased from ICN Biochemicals (Cleveland, Ohio). The nutrient composition of these diets is presented in Tables 1–3.

TABLE 1

Nutrient Composition of Test Diets (percent by weight)

|  | Protein | Carbohydrate | Fat |
| --- | --- | --- | --- |
| Normal | 18.3 | 67 | 5 |
| Fat free | 18.3 | 78.2 | 0 |
| Protein free | 0 | 83.1 | 5 |
| Carbohydrate free | 18.3 | 0 | 34 |
| 4% Protein | 4 | 79.6 | 4.95 |
| 8% Protein | 8 | 76.2 | 4.9 |
| 12% Protein | 12 | 72.7 | 4.86 |

All diets were supplemented with 3.5% AIN mineral mix (Table 2) and 1% AIN vitamin mix (Table 3). Alphacel, a nonnutritive additive available from ICN Biochemicals (Cleveland, Ohio), was included to make all diets comparable in caloric concentration (about 386 calories/100 g).

TABLE 2

Mineral Mix for AIN-76A Rodent Diet*
Use at 35 g/kg diet or
35 g/4000 kcal digestible energy

| Ingredient | g |  | Amount in 35 g |  |
| --- | --- | --- | --- | --- |
| Calcium Phosphate, Dibasic 79.5% Ca, 22.8% P | 500 | Ca P | 5.2 4.0 | g g |
| Magnesium Oxide 60.3% Mg | 24 | Mg | 0.5 | g |
| Potassium Citrate, 1 H$_2$O 36.2% K | 220 | K | 3.6 | g |
| Potassium Sulfate 44.9% K, 18.4% S | 52 | S | 0.33 | g |
| Sodium Chloride 39.3% Na, 60.7% Cl | 74 | Na Cl | 1.0 1.6 | g g |
| Chromium Potassium Sulfate, 12 H$_2$O 10.4% Cr | 0.55 | Cr | 2.0 | mg |
| Cupric Carbonate 57.5% Cu | 0.3 | Cu | 6.0 | mg |
| Potassium Iodate 59.3% I | 0.01 | I | 0.2 | mg |
| Ferric Citrate 21.2% Fe | 6.0 | Fe | 45 | mg |
| Manganous Carbonate 47.8% Mn | 3.5 | Mn | 59 | mg |
| Sodium Selenite 45.7% Se | 0.01 | Se | 0.16 | mg |
| Zinc Carbonate | 1.6 | Zn | 29 | mg |
| Sucrose | 118.03 |  |  |  |
| TOTAL | 1000. |  |  |  |

*J. Nutr. 107:1340–1348 (1977)

TABLE 3

Vitamin Mix for AIN-76A Rodent Diet*
Use at 10 g/kg diet or
10 g/4000 kcal digestible energy

| Ingredient | g | Amount in 10 g |  |
| --- | --- | --- | --- |
| Vitamin A Palmitate 500,000 IU/g | 0.9 | 4,000 | IU |
| Vitamin D$_3$ 100,000 IU/g | 1.0 | 1,000 | IU |
| Vitamin E Acetate 500 IU/g | 10.0 | 50 | IU |
| Menadione Sodium Bisulfite 62.5% Menadione | 0.08 | 0.5 | mg |
| Biotin, 1.0% | 2.0 | 0.2 | mg |
| Cyancocobalamin, 0.1% | 1.0 | 10 | μg |
| Folic Acid | 0.2 | 2 | mg |
| Nicotinic Acid | 3.0 | 30 | mg |
| Calcium Pantothenate 16 mg | 1.6 |  |  |
| Pyridoxine-HCl | 0.7 | 7 | mg |
| Riboflavin | 0.6 | 6 | mg |
| Thiamin HCl | 0.6 | 6 | mg |
| Sucrose | 978.42 |  |  |
| TOTAL | 1000. |  |  |

*J. Nutr. 107:1340–1348 (1977); J. Nutr. 110:1726 (1980)

To determine the effect of refeeding diets deficient in select nutrients to food deprived (FD) rats on levels of hypothalamic preproNPY mRNA, rats were allowed free access to food (Fed), FD for 72 h, or 72 h FD then refed for 72 h with either a normal (normal fed=NF; normal refed= NRF) diet or isocaloric diets free of fat (fat free=FF; fat free refed=FFRF), protein (protein free=PF; protein free refed= PFRF) or carbohydrate (carbohydrate free=CF; carbohydrate free refed=CFRF). The results are shown in FIG. 3.

Food deprivation resulted in a 2-fold increase in hypothalamic preproNPY mRNA. Upon refeeding, preproNPY mRNA levels were normalized by NRF, FFRF, and CFRF diets; however, the PF diet was without effect. Therefore further experiments were performed to evaluate dietary protein regulation of NPY gene expression.

Graded Protein Refeeding.

The effect of refeeding diets varying in protein composition on hypothalamic content of preproNPY mRNA was determined in groups of rats allowed free access to food or 72 h FD then refed isocaloric diets containing 4%, 8%, or 12% protein for 72 h. The results are shown in FIG. 4 and discussed below.

Select Amino Acid Refeeding.

Several possible mechanisms could account for the influence of the lack of dietary protein on hypothalamic NPY gene expression. One possibility is that protein deprivation might reduce or deplete amino acids necessary for neurotransmitter/neuropeptide synthesis. This experiment tested this hypothesis by measuring hypothalamic preproNPY mRNA in FD rats refed PF diets supplemented with individual amino acids directly involved in neuronal signal transmission or that serve as neurotransmitter precursors. Animals were adapted for 3–5 days to the facility at which time they were fed the same normal AIN 76A Semipurified Diet as before ad libitum for 3 days before the start of all experiments. Then they were divided into groups evenly matched for body weight. Protein free diets supplemented with individual amino acids contained each amino acid at the concentration found in the normal diet, i.e., 1.26% tyrosine, 0.30% tryptophan, 4.72% glutamic acid, and 0.60% histidine. All groups had free access to drinking water and were weighed before and after food deprivation and again after refeeding. Food consumption was monitored daily by subtracting uneaten food from total food given.

The effect of refeeding select amino acids added to a protein-free diet on hypothalamic content of preproNPY mRNA was determined in groups of rats FD then refed for 72 h with either a normal (NF) diet, an isocaloric diet free of protein (PF), or PF diets supplemented with tyrosine (Tyr), tryptophan (Trp), glutamic acid (GA) or histidine (His) and compared to groups of rats allowed free access to food (Fed) or FD. The results are shown in FIG. 5 and discussed below.

Tissue Handling

Rats were killed by decapitation and hypothalami rapidly dissected using landmarks to yield blocks weighing 20–25 mg as previously described (M. Berelowitz et al., "Effects of growth hormone excess and deficiency on hypothalamic somatostatin content and release and on tissue somatostatin distribution," Endocrinology 109:714–719 (1981)), then immediately frozen on dry ice for later RNA extraction.

RNA Extraction

Total hypothalamic RNA was isolated from dissected hypothalamic tissue blocks using methods developed previously (J. D. White et al., "Measurement of neuroendocrine peptide mRNA in discrete brain regions," Methods in Enzymology, P. M. Conn (Ed.), Academic Press, Orlando, Fla., 124:548–560 (1986)). RNA concentrations were estimated based on absorbance at 260 nm, and identical concentrations of RNA from each sample were used for nuclease protection. Aliquots (3–4 μg) of total RNA were electrophoresed in 1% agarose gel, stained with ethidium bromide, then examined visually to confirm quality and integrity and provide an estimate of quantity of RNA extracts.

Preparation of Probes

The $^{32}$P-labeled preproNPY cRNA probe was transcribed using T3 RNA polymerase from a 511-bp EcoR1 fragment of the NPY cDNA after linearization with PvuII (H. Higuchi et al., "Rat neuropeptide Y precursor gene expression," J Biol. Chem. 263:6288–6295 (1988)).

Nuclease Protection Assay

Solution hybridization/nuclease protection assays were performed as described using 5 μg total RNA from each hypothalamus (J. D. White et al., Measurement of neuroendocrine peptide mRNA in discrete brain regions," Methods in Enzymology, P. M. Conn (Ed.), Academic Press, Orlando, Fla., 124:548–560 (1986); J. F. Bruno et al., "Influence of food deprivation in the rat on hypothalamic expression of growth hormone-releasing factor and somatostatin," Endocrinology 127:2111–2116 (1990); J. F. Bruno et al., "Regulation of rat hypothalamic preprogrowth hormone-releasing factor messenger ribonucleic acid by dietary protein," Endocrinology 129:1226–1232 (1991)). After separation of stable hybrids on 8% polyacrylamide-8 M urea gels, the dried gels were exposed to Kodak (Rochester, N.Y.) X-Omat x-ray film to generate an autoradiograph; exposure times were from 24–72 h. Autoradiographic densities were quantitated using an LKB (Rockville, Md.) laser densitometer in the two dimensional scan mode to obtain a densitometric value for the entire autoradiographic band.

Analysis of Data

Results are expressed as the mean±SEM or SD, where indicated. Densitometric values were normalized to controls which were arbitrarily set to equal one. Comparisons of data between experimental groups were performed using one way analysis of variance, followed by Fisher's least significant difference test.

Results

Time Course

Total hypothalamic RNA was isolated from groups of rats food deprived for 24, 48, or 72 h and preproNPY mRNA content estimated using solution hybridization/nuclease protection assay. As shown in FIG. 1, hypothalamic preproNPY mRNA was increased by 30% as early as 24 h of food deprivation with maximal increases of 2.5 fold observed by 48 h.

Refeeding

FIG. 2 presents the effect of refeeding on hypothalamic preproNPY mRNA levels. Animals deprived of food for 72 h displayed over a 2 fold increase in preproNPY mRNA levels. Upon refeeding, preproNPY mRNA levels were restored to approximately 1.5 fold of fed levels after 24 h and were completely restored to fed values after 48 h.

Select Nutrient Refeeding

The effect of refeeding diets deficient in fat, protein, or carbohydrate to 72 h FD rats on hypothalamic preproNPY mRNA content is shown in FIG. 3. As shown, 72 h FD rats displayed the expected 2 fold increase in hypothalamic preproNPY mRNA. Refeeding 72 h FD rats NRF, FFRF, or CFRF diets completely restored preproNPY mRNA levels to fed controls. PreproNPY mRNA levels in rats refed a PFRF diet, however, were not significantly different from 72 h FD rats.

Graded Protein Refeeding.

To further investigate the regulation of hypothalamic preproNPY mRNA by dietary protein, groups of 72 h FD rats were refed diets containing 4%, 8%, or 12% protein (PRF) for 72 h. As shown in FIG. 4, hypothalamic preproNPY mRNA levels were increased 2-fold in 72 h FD rats.

Upon refeeding, preproNPY mRNA levels remained elevated in rats fed a PFRF diet, whereas feeding diets varying in protein content restored preproNPY mRNA levels to Fed values.

Amino Acid Refeeding.

The effect of refeeding PF diets supplemented with select amino acids to FD rats on hypothalamic preproNPY mRNA content is shown in FIG. 5. As shown, preproNPY mRNA levels were increased two-fold in FD rats and refeeding a normal diet (NRF) restored preproNPY mRNA levels towards fed control values. However, refeeding a PF diet alone (PFRF) or a PFRF diet with added Tyr, His or GA were without effect. In contrast, preproNPY mRNA levels were restored to fed values by a PFRF diet supplemented with Trp.

Discussion and Significance

Results from these studies demonstrated that food-deprived rats show a dramatic increase in hypothalamic preproNPY mRNA levels occurring as a result of dietary protein restriction. Rats food-deprived for 72 h (FD) demonstrated an increase in hypothalamic preproNPY mRNA levels by over two-fold compared to fed controls. Refeeding FD rats restored preproNPY mRNA levels to control values by 48 h.

In addition, the data indicate that increased hypothalamic preproNPY mRNA expression in FD rats occurs as a result of dietary protein deprivation. Refeeding FD rats a normal (NRF) diet, or protein-containing fat free (FFRF) or carbohydrate free (CFRF) diets normalized hypothalamic preproNPY mRNA levels while those refed a protein free (PFRF) diet demonstrated preproNPY mRNA levels similar to those in FD rats. Isocaloric diets containing 4%, 8% or 12% protein fed to FD rats restored preproNPY mRNA to fed values.

Furthermore, the inventors have identified tryptophan as a major component of dietary protein involved in regulating NPY gene expression. The results of the studies of this example clearly show that when FD rats are refed PF diets supplemented with individual amino acids that serve as neurotransmitters or neurotransmitter precursors, only tryptophan could restore preproNPY mRNA levels toward control values. PF diets containing Tyr, His or GA failed to restore levels above that seen with a PF diet alone (i.e., levels not significantly different than FD rats).

Thus, the results of these studies coupled with the previous finding that hypothalamic GRF expression is regulated by the amino acid histidine, and the additional finding in the following Example 2, led to the formulation of the preferred diet identified herein, i.e., a low calorie, low protein diet containing tryptophan to maintain NPY at levels to control the drive to eat and histidine at levels to regulate GRF and restore plasma growth hormone, thus promoting lipolysis, i.e., breaking down fat instead of muscle protein.

EXAMPLE 2

The Animals Used in This Study

Thirty male Sprague Dawley rats weighing 273±10 g were placed on a high calorie, high fat diet (4.8 kcal/gm, 46% of calories derived from fat) in order to render them obese. This method of generating obesity was chosen over other available genetic models since it best mimics the most common natural form of obesity in humans.

To assess obesity, a control group of rats weighing 268±13 g was maintained under identical housing conditions with the exception that the control group was fed a diet comprising standard laboratory rat chow (Ralston-Purina, St. Louis, Mo.). After 16 weeks, the average weight of the control group was 521 g with a standard deviation of 24 g. Obesity in rats is defined as that weight which exceeds the mean weight of a control group by at least two standard deviations. Thus, in this experiment a rat was considered to be obese when the total body weight of the animal was at least 50 g more than the mean weight of control rats. This control group was used to determine the weight of animals during the course of the experiment that were not fed the high fat diet. Thus, obese Sprague-Dawley rats should weigh at least 571 g. Using this definition, twenty of the original thirty Sprague Dawley rats which were maintained on the high calorie, high fat diet were obese with a mean weight 615±38 g. These were selected as the test group of animals.

The Diets

Standard laboratory rat chow comprises approximately 20% protein, 65% carbohydrate, 5% fat, 5% cellulose and 5% vitamin and mineral supplements. This diet was used as a basis for constructing two isocaloric experimental diets which were modified to contain 6.7% protein, 76.6% carbohydrate, 5% fat, 5% cellulose and 5% vitamin and mineral supplements. This same basic diet was fed to all animals, i.e., all animals had vitamins and minerals. This low protein diet served as a low protein level to which the specific amino acids tryptophan and histidine were added. Table 4 below reflects the formulation of the diet.

Two formulations of this low protein diet were made which were designated as Low Protein+[LP(+)] and Low Protein−[LP(−)]. LP(+) was supplemented with 0.5% L-tryptophan, 0.83% L-histidine and 0.6% L-arginine. LP(−) was supplemented with phenylalanine and valine at levels approximating the combined amount of tryptophan, histidine and arginine present in the LP(+) diet, i.e., 0.9% of each amino acid, without exceeding the normal physiological levels.

TABLE 4

Formulation of Diets LP(+) and LP(−)

|  | Diet LP(+) | | Diet LP(−) | |
| --- | --- | --- | --- | --- |
|  | % (g) | % (kcal) | % (g) | % (kcal) |
| Protein | 8.7 | 8.8 | 8.1 | 8.3 |
| Carbohydrate | 77.6 | 79.6 | 78.2 | 80.2 |
| Fat | 5.0 | 11.5 | 5.0 | 11.5 |
| Total | 91.3 | 100.0 | 91,3 | 100.0 |
| kcal/gm | 3.90 | | 3.90 | |
| Ingredients: | gm | kcal | gm | kcal |
| Casein, 80 Mesh | 66.7 | 266.8 | 66.7 | 266.8 |
| DL-Methionine | 1 | 0 | 1 | 0 |
| Maltodextrin 10 | 150 | 600 | 150 | 600 |
| Corn Starch | 616 | 2464 | 617 | 2469 |
| Sucrose | 0 | 0 | 0 | 0 |
| Cellulose, BW200 | 50 | 0 | 50 | 0 |
| Corn Oil | 50 | 450 | 50 | 450 |
| Salt Mix S10001 | 35 | 0 | 35 | 0 |
| Vitamin Mix V10001 | 10 | 40 | 10 | 40 |
| Choline Bitartrate | 2 | 0 | 2 | 0 |
| L-Tryptophan | 5 | 20 | 0 | 0 |
| L-Histidine | 8.3 | 33.2 | 0 | 0 |
| L-Arginine | 6 | 24 | 0 | 0 |
| L-Phenylalanine | 0 | 0 | 9 | 36 |
| L-Valine | 0 | 0 | 9 | 36 |

TABLE 4-continued

Formulation of Diets LP(+) and LP(-)

|  | Diet LP(+) | | Diet LP(-) | |
|---|---|---|---|---|
| FD&C Red Dye #40 | 0 | 0 | 0.1 | 0 |
| FD&C Blue Dye #1 | 0.1 | 0 | 0 | 0 |
| FD&C Yellow Dye #5 | 0 | 0 | 0 | 0 |
| Total | 1000.1 | 3898 | 1000.1 | 3898 |

Test Group of Animals

The twenty obese test animals were randomly divided into four groups as follows:

Group A consisted of five animals which were fed the LP(-) diet ad libitum.

Group B consisted of five animals which were fed the LP(+) diet ad libitum.

Group C consisted of five animals which were fed the LP(-) diet on a calorically restricted basis, i.e., 18 g/rat/day, representing approximately 70% of the normal caloric intake of the control group being fed standard laboratory rat chow ad libitum.

Group D consisted of five animals which were fed the LP(+) diet on a calorically restricted basis, i.e., 18 g/rat/day, representing approximately 70% of the normal caloric intake of the control group being fed standard laboratory rat chow ad libitum.

Measurement of Body Weight, Food Consumption, Appetite and Body Fat in the Animals The weight of the animals from Groups A, B, C, and D were determined weekly using a standard laboratory scale designed to weigh small animals.

The amount of food (g/rat/day) consumed by animals fed LP(-) and LP(+) diets ad libitum was assessed on a weekly basis.

Measurements of appetite in rats was accomplished by assessing their willingness to take additional food. Refusal to eat additional food is an indication of satiation and absence of hunger. Hyperphagia is defined herein as a statistically signification increase in the weight of food consumed within a defined period of time by a test animal compared with a control animal.

Appetite was measured in Group C and D animals by assessing the amount of food which was consumed over specific time periods following presentation of the food to the animals. All animals were fed a measured amount (18 g) of the appropriate LP diet once per day at 09:00 h (lights out). Two hours after the food was provided to the animals, the amount of uneaten food was weighed. Animals were then allowed to continue consumption of the food for an additional two hours, at which time the amount of food remaining was again weighed. Thus, appetite was assessed as a measure of the amount and rate of food consumption during a four hour period following presentation of the food to the animals.

The metabolic rate of an animal is assessed by measuring the amount of lean tissue versus fatty tissue catabolized by the animal following the diet period. Thus, total body weight and fat content were measured at the end of the dietary period. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

Isolation of Hypothalamic Blocks and RNA Extraction

After sacrificing the animals, hypothalami were rapidly dissected using landmarks to yield blocks weighing 20–25 mg and total hypothalamic RNA was isolated using guanidine isothiocyanate as previously described in Berelowitz et al. (1981), supra, and White et al. (1986), supra. RNA concentrations were estimated based on absorbance at 260 nm, and identical concentrations of RNA from each sample were used for nuclease protection. Aliquots (3–4 $\mu$g) of total RNA were electrophoresed in 1% agarose gel, stained with ethidium bromide, then examined visually to confirm quality and integrity and provide an estimate of quantity of RNA extracts.

Preparation of Probes

GRF cDNA constructs in pGEM 3, and NPY cDNA constructs in pBS M13(-) were used to generate $^{32}$P-labeled antisense RNA for nuclease protection assays. The prepro-GRF cRNA probe was transcribed in the presence of SP6 polymerase from a 215-base pair (bp) EcoRI-HindIII fragment of the rat cDNA provided by Kelly E. Mayo (Northwestern University) after linearization with EcoRi (K. E. Mayo et al., "Characterization of cDNA and genomic clones encoding the precursor of rat hypothalamic growth hormone-releasing factor," Nature 314:464–467 (1985)). The $^{32}$P-labeled prepro-NPY cRNA probe was transcribed using T3 RNA polymerase from a 511-bp EcoR1 fragment of the NPY cDNA after linearization with PvuII (Higuchi et al. (1988), supra).

Nuclease Protection Assay

Solution hybridization/nuclease protection assays were performed as described using 5 $\mu$g total RNA from each hypothalamus (White et al. (1986), supra, Bruno et al. (1990) supra, and Bruno et al. (1991), supra). After separation of stable hybrids on 8% polyacrylamide-8 M urea gels, the dried gels were exposed to Kodak (Rochester, N.Y.) X-Omat x-ray film to generate an autoradiograph; exposure times were from 24–72 h. Autoradiographic densities were quantitated using an LKB (Rockville, Md.) laser densitometer in the two dimensional scan mode to obtain a densitometric value for the entire autoradiographic band.

Analysis of Data

Results are expressed as the mean±SEM or SD, where indicated. Densitometric values were normalized to controls which were arbitrarily set to equal one. Comparisons of data between experimental groups were performed using Student's T-test or one way analysis of variance, followed by Fisher's least significant difference test.

RESULTS

Group A and Group B. ad libitum Fed Rats.

Changes in body weight

Obese male Sprague Dawley rats were randomly assigned to one of two groups. Rats in Group A having an initial body weight of 625±16 g were fed the LP(-) diet while animals assigned to Group B had an initial body weight of 591±10 g and were fed the LP(+) diet. Both groups received the diet ad libitum for seven weeks and body weight changes were monitored weekly. As shown in FIG. 6, body weight of both groups fluctuated over time, however, neither the body weight changes over the seven week period nor the initial body weight of Group A was significantly different from Group B.

Food Consumption

Food consumption data for Groups A and B are presented in FIG. 7. Overall, there was a tendency for Group B to consume less food than Group A. In week six of the study, the amount of food consumed by the two groups was significantly different with Group A consuming an average of 23.4 g/rat/day vs. 21.3 g/rat/day for group B, p<0.05.

Retroperitoneal Fat Pads

Retroperitoneal fat pad weight for obese rats fed ad libitum diets LP(−) and LP(+) is presented in FIG. 8. The fat pad of Group A weighed 1.2 g more than that of Group B (18.3±0.5 g for Group A vs. 17.1±0.5 g for Group B), however, this difference was not significant.

Groups C and D, Food Restricted Groups

Body weight changes

In this set of experiments, groups of rats were food restricted to mimic the low caloric intake of humans on a low calorie diet. Thus, ten obese rats were randomly assigned to one of two groups. Rats assigned to Group C had an initial body weight of 620±20 g while animals in Group D weighed 625±20 g. Group C rats were fed diet LP(−) and Group D rats were fed LP(+) at 18 g/rat/day, representing approximately 70% of the normal caloric intake of the control group being fed standard laboratory rat chow ab libitum, for 7 weeks. As shown in FIG. 9, animals in both groups rapidly lost weight with a similar 30 g average weight loss observed in both groups after 2 weeks of food restriction. However, by week 3, weight loss began to diverge with Group D loosing weight at a faster rate than Group C. Indeed, the total weight lost by Group D in weeks 6 and 7 was significantly different than that lost by Group C. Overall, after 7 weeks of food restriction, Group D lost a total of 69 g of weight compared to 53 g by group C (p<0.05).

Appetite

To measure appetite, i.e., the drive to eat food, consumption was measured in Groups C and D by assessing the amount of food consumed within specific time periods following presentation of food to the animals. Rats were fed 18 g of the appropriate LP diet once per day at 09:00 h (lights out) and the amount of uneaten food was weighed two and four hours later over a fourteen day period. Thus, appetite was assessed as a measure of the amount and rate of food consumption during this four hour period. As shown in FIG. 10, animals fed the LP(+) diet ate significantly less food than animals fed the LP(−) diet two and four hours after food presentation. Two hours after food presentation, rats fed the LP(+) diet ate an average of 8.9±1.3 g of food compared to 11.1±2.3 g for the LP (−) rats (p<0.05), a difference of 2.2 g. At four hours the difference was even greater: the LP(+) rats ate an average of 13.3±1.3 g vs. 16.1±0.7 g for the LP(−) group, a difference of 2.8 g (p<0.001).

Measurement of Total Body Fat

Retroperitoneal fat pad weight of rats in Groups C and D is presented in FIG. 11. As shown, fat pad weight tended to be higher in rats fed the LP(−) diet having a mean weight of 16.4 g compared to an average pad weight of 14.8 g for rats fed the LP(+) diet, a difference of 1.6 g.

Hypothalamic peproGRF mRNA and preproNPY mRNA Expression

The effect of feeding rats diets LP(−) and LP(+) on hypothalamic preproGRF mRNA and preproNPY mRNA content is shown in FIGS. 12 and 13, respectively. As shown, preproGRF mRNA levels were reduced in rats fed the LP(−) diet relative to levels in rats fed the LP(+) diet (FIG. 12). Levels of preproNPY mRNA in rats fed the LP(−) diet, however, were elevated compared to rats fed the LP(+) diet (FIG. 13).

Conclusion and Significance

Control of food intake, body weight and metabolism depends on a complex set of interrelated processes that, ultimately, are controlled through the actions of the central nervous system. However, control by the brain of these behaviors and physiological parameters is determined by the interaction of peripheral metabolic signals that are recognized by the brain and then acted upon appropriately. Thus, defining the neural systems through which food intake and metabolism are controlled as well as the signals to which these systems respond are of critical importance to understanding control of feeding and metabolism. Two neural systems implicated in controlling these processes have been identified. The first system is NPY which is one of the most potent naturally occurring substances that can stimulate feeding. The second system is GRF. This peptide regulates growth hormone secretion which in adults acts as a principal metabolic regulatory hormone promoting lipolysis while inhibiting protein breakdown. In experimental models of aberrant metabolic homeostasis associated with hyperphagia, i.e., in models analogous to human obesity, NPY and GRF are regulated in parallel but opposite direction. Thus, NPY levels are elevated stimulating the drive to eat and GRF levels are depressed which is associated with reduced plasma growth hormone levels and reduction in lipolysis and metabolic rate. The inventors have demonstrated that the levels of these two neurotransmitters can be regulated by specific amino acids. For NPY the critical amino acid is tryptophan, while the critical amino acid for GRF is histidine.

It is the major hypothesis underlying this invention that all current diets schemes are destined for failure because they do not effectively eliminate the drive to eat that originates in the central nervous system through elevated NPY. Moreover, current diets do not effectively utilize endogenous hormones such as GRF to promote lipolysis and maintain nitrogen balance via regulation of growth hormone. The diet formulation for this invention addresses both of these pitfalls through a unique combination of nutrients supplemented with amino acids. This diet will not only facilitate weight loss like other currently available diets, but the unique formulation of the present invention will also regulate appetite and maintain a positive nitrogen balance in the face of a low caloric intake.

The experimental data presented herein support the conclusion of these experiments that feeding rats the LP(+) diet, i.e., a low calorie, low protein diet supplemented with the amino acids tryptophan and histidine, had a dramatic effect on appetite and metabolism when compared to animals fed an identical diet lacking these supplements.

Animals fed the LP(+) diet on an ad libitum basis tended to gain less weight, to eat less and to have less fat. However, the major and most dramatic findings were observed when animals were fed both test diets on a restricted regimen. Thus, animals fed the LP(+) diet at 18 g/rat/day lost more weight than rats fed the same amount (i.e., the same number of calories) of the LP(−) diet. The most likely explanation for this startling finding is that the LP(+) diet had a major effect on the metabolic rate of the animal, as predicted. Thus, a higher basal metabolic rate would require more calories and over time result in a greater loss of weight.

Animals fed the LP(+) diet had a decreased drive to eat as measured by food consumed within a given time period which can be attributed to tryptophan regulation of hypothalamic levels of NPY, thus confirming another major aspect of this invention.

Another major aspect of this invention is that supplementation with histidine regulates GRF levels and normalizes plasma growth hormone levels, thus promoting lipolysis while inhibiting protein breakdown. Rats fed the LP(+) diet had less overall body fat as measured by retroperitoneal fat pad weight.

Perhaps the most conclusive evidence as to the efficacy of this invention is the nuclease protection data measuring hypothalamic preproNPY mRNA and preproGRF mRNA levels. The data support the conclusion that body weight, appetite and total body fat were being regulated by these neurotransmitters, which in turn were being regulated by the amino acids supplemented in the LP(+) diet, as determined by reduced hypothalamic levels of preproNPY mRNA while preproGRF mRNA levels increased in animals fed the LP(+) diet.

Thus, when obese rats were fed a unique diet supplemented with amino acids that regulate the NPY and GRF neural systems, they experience greater weight loss, their appetite is better regulated and they have less overall body fat when compared to a second group of like obese animals fed the same number of calories of a similar diet lacking these key amino acids.

Development of a superior diet scheme that results in better, long term weight control while controlling appetite and minimizing the risk of muscle wasting is of obvious clinical significance. Such a diet will greatly benefit a large number of obese individuals with consequent, secondary benefits to their health, well-being, productivity and reduced societal burdens. This diet may prove to be particularly important in the treatment of obese patients suffering from Type II diabetes mellitus in whom renal complications will be exacerbated using typical high protein-hypocaloric diets. The diet formulation contained in this invention is such a diet.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method of reducing an animal's drive to eat comprising administering to the animal a diet comprising a lower amount of calories and protein than in a pre-administration diet prior to administering the lower calorie, lower protein diet, and orally supplementing the diet with an appetite-reducing amount of tryptophan sufficient to reduce the animal's level of neuropeptide Y compared to a pre-administration level of neuropeptide Y.

2. A method of weight control in an animal comprising administering to the animal a diet comprising a lower amount of calories and protein than in a pre-administration diet prior to administering the lower calorie, lower protein diet, and orally supplementing the diet with an appetite-reducing amount of tryptophan sufficient to reduce the animal's level of neuropeptide Y compared to a pre-administration level of neuropeptide Y.

3. A method of stabilizing an animal's metabolic rate comprising administering to the animal a diet comprising a lower amount of calories and protein than in a pre-administration diet prior to administering the lower calorie, lower protein diet, and supplementing the diet with an amount of histidine sufficient to elicit an increase of a metabolic rate-stabilizing amount of growth hormone releasing factor in the animal to a level compared to a pre-administration level of growth hormone releasing factor.

4. A method of weight control in an animal comprising administering to the animal a diet comprising a lower amount of calories and protein than in a pre-administration diet prior to administering the lower calorie, lower protein diet, and supplementing the diet with an amount of histidine sufficient to elicit an increase of a metabolic rate-stabilizing amount of growth hormone releasing factor in the animal compared to a pre-administration level of growth hormone releasing factor.

5. A method of reducing an animal's drive to eat and increasing the animal's metabolic rate comprising administering to the animal a diet comprising a lower amount of calories and protein than in a pre-administration diet prior to administering the lower calorie, lower protein diet, and supplementing the diet with an appetite-reducing amount of tryptophan sufficient to reduce the animal's level of neuropeptide Y compared to a pre-administration level of neuropeptide Y and with an amount of histidine sufficient to elicit an increase of a metabolic rate-stabilizing amount of growth hormone releasing factor in the animal compared to a pre-administration level of growth hormone releasing factor.

6. A method of weight control in an animal comprising administering to the animal a diet comprising a lower amount of calories and protein than in a pre-administration diet prior to administering the lower calorie, lower protein diet, and supplementing the diet with an appetite-reducing amount of tryptophan sufficient to reduce the animal's level of neuropeptide Y compared to a pre-administration level of neuropeptide Y and with an amount of histidine sufficient to elicit an increase of a metabolic rate-stabilizing amount of growth hormone releasing factor in the animal compared to a pre-administration level of growth hormone releasing factor.

7. A method according to any one of claims 1 through 6 wherein the lower calorie, lower protein diet has no more than about 85% calories and protein than the pre-administration diet.

8. A method according to any one of claims 1 through 6 wherein the lower calorie, lower protein diet has no more than about 70% of the calories and protein than the pre-administration diet.

9. A method of controlling secretion of neuropeptide Y in an animal comprising administering to the animal, at a controlled release rate, a neuropeptide Y-modulating amount of tryptophan sufficient to elicit a reduced level of neuropeptide Y over a sustained period of at least about 4 hours.

10. A method of controlling the secretion of neuropeptide Y and growth hormone releasing factor in an animal comprising administering to the animal, at a controlled release rate, a neuropeptide Y-modulating amount tryptophan and a growth hormone releasing factor-modulating amount of histidine sufficient to elicit a respective reduced level of neuropeptide Y and an increased level of growth hormone releasing factor, compared to pre-administration levels of neuropeptide Y and growth hormone releasing factor, over a sustained period of at least about 4 hours.

11. A method according to any one of claims 1 through 6, 9 and 10, wherein the animal is a human.

12. A human food composition for controlling weight wherein the composition comprises a daily diet of less than about 2,400 calories, about 10 g to about 540 g of protein and about 5 mg to about 125 mg of tryptophan per g of protein.

13. A human food composition according to claim 12 wherein the composition comprises a daily diet of about 800 to about 1,200 calories, about 10 g to about 270 g of protein and about 6 mg to about 61 mg of tryptophan per g of protein.

14. A human food composition according to claim 12 wherein the composition comprises a daily diet of less than about 800 calories, about 10 g to about 180 g of protein and about 8 mg to about 31 mg of tryptophan per g of protein.

15. A human food composition according to claim 12 wherein the composition comprises a daily diet of less than about 2,400 calories, about 10 g to about 540 g of protein, about 60 g to about 540 g of carbohydrate, about 2 g to about 240 g of fat, and about 5 mg to about 125 mg of tryptophan per g of protein.

16. A human food composition according to claim 12 wherein the composition comprises a daily diet of about 800 to about 1,200 calories, about 10 g to about 270 g of protein, about 30 g to about 270 g of carbohydrate, about 1 g to about 120 g of fat, and about 6 mg to about 61 mg of tryptophan per g of protein.

17. A human food composition according to claim 12 wherein the composition comprises a daily diet of less than about 800 calories, about 10 g to about 180 g of protein, about 20 g to about 180 g of carbohydrate, about 0.5 g to about 80 g of fat, and about 8 mg to about 31 mg of tryptophan per g of protein.

18. A human food composition for controlling weight wherein the composition comprises a daily diet of less than about 2,400 calories, about 10 g to about 540 g of protein and about 10 mg to about 270 mg of histidine per g of protein.

19. A human food composition according to claim 18 wherein the composition comprises a daily diet of about 800 to about 1,200 calories, about 10 g to about 270 g of protein and about 15 mg to about 135 mg of histidine per g of protein.

20. A human food composition according to claim 18 wherein the composition comprises a daily diet of less than about 800 calories, about 10 g to about 180 g of protein and about 17 mg to about 68 mg of histidine per g of protein.

21. A human food composition according to claim 18 wherein the composition comprises a daily diet of less than about 2,400 calories, about 10 g to about 540 g of protein, about 60 g to about 540 g of carbohydrate, about 2 g to about 240 g of fat, and about 10 mg to about 270 mg of histidine per g of protein.

22. A human food composition according to claim 18 wherein the composition comprises a daily diet of about 800 to about 1,200 calories, about 10 g to about 270 g of protein, about 30 g to about 270 g of carbohydrate, about 1 g to about 120 g of fat, and about 15 mg to about 135 mg of histidine per g of protein.

23. A human food composition according to claim 18 wherein the composition comprises a daily diet of less than about 800 calories, about 10 g to about 180 g of protein, about 20 g to about 180 g of carbohydrate, about 0.5 g to about 80 g of fat, and about 17 mg to about 68 mg of histidine per g of protein.

24. A human food composition for controlling weight wherein the composition comprises a daily diet of less than about 2,400 calories, about 10 g to about 540 g of protein, about 5 mg to about 125 mg of tryptophan per g of protein and about 10 mg to about 270 mg of histidine per g of protein.

25. A human food composition according to claim 24 wherein the composition comprises a daily diet of about 800 to about 1,200 calories, about 10 g to about 270 g of protein, about 6 mg to about 61 mg per g of protein and about 15 mg of tryptophan to about 135 mg of histidine per g of protein.

26. A human food composition according to claim 24 wherein the composition comprises a daily diet of less than about 800 calories, about 10 g to about 180 g of protein, about 8 mg to about 31 mg tryptophan per g of protein and about 17 mg to about 68 mg of histidine per g of protein.

27. A human food composition according to claim 24 wherein the composition comprises a daily diet of less than about 2,400 calories, about 10 g to about 540 g of protein, about 60 g to about 540 g of carbohydrate, about 2 g to about 240 g of fat, about 5 mg to about 125 mg per g of protein and about 10 mg of tryptophan to about 270 mg of histidine per g of protein.

28. A human food composition according to claim 24 wherein the composition comprises a daily diet of about 800 to about 1,200 calories, about 10 g to about 270 g of protein, about 30 g to about 270 g of carbohydrate, about 1 g to about 120 g of fat, about 6 mg to about 61 mg of tryptophan per g of protein and about 15 mg to about 135 mg of histidine per g of protein.

29. A human food composition according to claim 24 wherein the composition comprises a daily diet of less than about 800 calories, about 10 g to about 180 g of protein, about 20 g to about 180 g of carbohydrate, about 0.5 g to about 80 g of fat, about 8 mg to about 31 mg of tryptophan per g of protein and about 17 mg to about 68 mg of histidine per g of protein.

30. A method according to any one of claims 1 through 6, 9 and 10, wherein the animal is a human, and wherein the diet is supplemented with about 5 mg to about 125 mg of tryptophan per g of protein.

31. A method according to any one of claims 1 through 6, 9 and 10, wherein the animal is a human, and wherein the diet is supplemented with about 10 mg to about 270 mg of histidine per g of protein.

32. A method according to any one of claims 1 through 6, 9 and 10, wherein the animal is a human, and wherein the diet is supplemented with about 5 mg to about 125 mg of tryptophan per g of protein and about 10 mg to about 270 mg of histidine per g of protein.

* * * * *